(12) United States Patent
Walker

(10) Patent No.: US 9,610,084 B2
(45) Date of Patent: Apr. 4, 2017

(54) METHOD AND APPARATUS FOR HIP REPLACEMENTS

(71) Applicant: Peter Michael Sutherland Walker, Bellevue Hill (AU)

(72) Inventor: Peter Michael Sutherland Walker, Bellevue Hill (AU)

( * ) Notice: Subject to any disclaimer, the term of this patent is extended or adjusted under 35 U.S.C. 154(b) by 342 days.

(21) Appl. No.: 14/024,600

(22) Filed: Sep. 11, 2013

(65) Prior Publication Data

US 2014/0107652 A1    Apr. 17, 2014

(51) Int. Cl.
| | | |
|---|---|---|
| A61B 17/00 | (2006.01) | |
| A61B 17/16 | (2006.01) | |
| A61B 17/17 | (2006.01) | |
| A61B 17/15 | (2006.01) | |

(52) U.S. Cl.
CPC .......... *A61B 17/1666* (2013.01); *A61B 17/15* (2013.01); *A61B 17/1617* (2013.01); *A61B 17/1668* (2013.01); *A61B 17/1742* (2013.01); *A61B 17/1746* (2013.01)

(58) Field of Classification Search
None
See application file for complete search history.

(56) References Cited

U.S. PATENT DOCUMENTS

| | | |
|---|---|---|
| 3,955,568 A | 5/1976 | Neufeld |
| 4,552,136 A | 11/1985 | Kenna |
| 5,007,936 A | 4/1991 | Woolson |
| 5,156,626 A | 10/1992 | Broderick et al. |
| 5,342,366 A | 8/1994 | Whiteside et al. |
| 5,364,403 A | 11/1994 | Petersen et al. |
| 5,769,092 A | 6/1998 | Williamson, Jr. |
| 5,885,297 A | 3/1999 | Matsen, III |
| 6,010,535 A | 1/2000 | Shah |

(Continued)

FOREIGN PATENT DOCUMENTS

| | | |
|---|---|---|
| AU | 2005200196 A1 | 2/2005 |
| CA | 2467800 A1 | 8/2003 |

(Continued)

OTHER PUBLICATIONS

Internet Archive Wayback Machine of www.superpathhiptechnique.com with image captured on Dec. 15, 2012.

(Continued)

*Primary Examiner* — Sameh Boles
(74) *Attorney, Agent, or Firm* — Clayton, Howarth & Cannon, P.C.

(57) ABSTRACT

A hip replacement method in which includes making an anterior incision and a lateral incision proximate the hip joint. The method next includes preparing a femoral passage directed along an axis of the femoral neck of the femur. An acetabulum reamer coupled to a femoral elongate element installed in the femoral passage is used to ream the acetabulum. The femoral head is prepared using a tool coupled to a femoral elongate element installed in the femoral passage. An acetabular prosthesis is then installed using a femoral elongate element installed in the femoral passage. A femoral prosthesis is installed using a femoral elongate element installed in the femoral passage. All of the foregoing steps are performed without dislocating the hip joint.

36 Claims, 30 Drawing Sheets

(56) References Cited

U.S. PATENT DOCUMENTS

| | | |
|---|---|---|
| 6,162,227 A | 12/2000 | Eckhardt et al. |
| 6,231,611 B1 | 5/2001 | Mosseri |
| 6,284,002 B1 | 9/2001 | Sotereanos |
| 6,589,281 B2 | 7/2003 | Hyde, Jr. |
| 6,626,948 B2 | 9/2003 | Storer et al. |
| 6,676,706 B1 | 1/2004 | Mears et al. |
| 6,695,850 B2 | 2/2004 | Diaz |
| 6,695,883 B2 | 2/2004 | Crofford |
| 6,723,102 B2 | 4/2004 | Johnson et al. |
| 6,755,865 B2 | 6/2004 | Tarabishy |
| 6,855,149 B2 | 2/2005 | Dye |
| 6,860,903 B2 | 3/2005 | Mears et al. |
| 6,875,218 B2 | 4/2005 | Dye et al. |
| 6,918,914 B2 | 7/2005 | Bauer |
| 6,953,480 B2 | 10/2005 | Mears et al. |
| 6,991,656 B2 | 1/2006 | Mears |
| 7,004,972 B2 | 2/2006 | Yoon |
| 7,037,310 B2 | 5/2006 | Murphy |
| 7,097,646 B2 | 8/2006 | Schantz |
| 7,105,028 B2 | 9/2006 | Murphy |
| 7,172,554 B2 | 2/2007 | Gustke et al. |
| 7,247,158 B2 | 7/2007 | Harris, Jr. |
| 7,338,499 B1 | 3/2008 | Kuczynski et al. |
| 7,455,674 B2 | 11/2008 | Rose |
| 7,559,928 B2 | 7/2009 | Johnson et al. |
| 7,591,821 B2 | 9/2009 | Kelman |
| 7,641,699 B2 | 1/2010 | Unger |
| 7,695,474 B2 | 4/2010 | Crofford |
| 7,780,669 B2 | 8/2010 | Lechot et al. |
| 7,780,673 B2 | 8/2010 | Acker et al. |
| 7,833,228 B1 | 11/2010 | Hershberger |
| 7,833,275 B2 | 11/2010 | Mears et al. |
| 7,854,769 B2 | 12/2010 | Hershberger |
| 7,909,881 B2 | 3/2011 | Boucher et al. |
| 7,914,584 B2 | 3/2011 | Bigsby et al. |
| 7,942,879 B2 | 5/2011 | Christie et al. |
| 7,976,545 B2 | 7/2011 | Hershberger et al. |
| D648,850 S | 11/2011 | Kelman |
| 8,066,779 B2 | 11/2011 | Gibbs et al. |
| 8,152,855 B2 | 4/2012 | Tulkis et al. |
| 8,211,183 B2 | 7/2012 | Podolsky |
| 8,236,004 B2 | 8/2012 | Jonas |
| 8,271,066 B2 | 9/2012 | Sarin et al. |
| D677,384 S | 3/2013 | Kelman |
| 8,512,345 B2 | 8/2013 | Bastian et al. |
| 8,579,985 B2 | 11/2013 | Podolsky et al. |
| 2002/0138148 A1 | 9/2002 | Hyde, Jr. |
| 2003/0050645 A1 | 3/2003 | Parker et al. |
| 2003/0100905 A1 | 5/2003 | Mears |
| 2003/0130741 A1 | 7/2003 | McMinn |
| 2003/0158559 A1 | 8/2003 | Diaz |
| 2004/0092949 A1 | 5/2004 | Dye et al. |
| 2005/0043805 A1* | 2/2005 | Chudik ............. A61B 17/1684 623/19.14 |
| 2005/0043810 A1 | 2/2005 | Mears et al. |
| 2005/0154398 A1 | 7/2005 | Miniaci et al. |
| 2005/0203384 A1 | 9/2005 | Sati et al. |
| 2006/0015188 A1 | 1/2006 | Grimes |
| 2006/0235539 A1 | 10/2006 | Blunn et al. |
| 2007/0213833 A1 | 9/2007 | Mears et al. |
| 2008/0255565 A1 | 10/2008 | Fletcher |
| 2008/0306601 A1 | 12/2008 | Dreyfuss |
| 2009/0076619 A1 | 3/2009 | Grappiolo et al. |
| 2009/0281545 A1 | 11/2009 | Stubs |
| 2011/0152868 A1 | 6/2011 | Kourtis et al. |
| 2012/0010723 A1 | 1/2012 | Walter et al. |
| 2012/0203352 A1 | 8/2012 | Perez, III et al. |
| 2012/0226361 A1 | 9/2012 | Podolsky |
| 2013/0053856 A1 | 2/2013 | Penenberg |
| 2013/0053858 A1 | 2/2013 | Penenberg |
| 2013/0053904 A1 | 2/2013 | Penenberg |
| 2014/0074250 A1 | 3/2014 | Podolsky et al. |

FOREIGN PATENT DOCUMENTS

| | | |
|---|---|---|
| CA | 2456602 A1 | 8/2004 |
| CA | 2623614 A1 | 4/2007 |
| CA | 2817207 A1 | 5/2012 |
| EP | 0086883 A1 | 2/1982 |
| EP | 0139356 A1 | 2/1985 |
| EP | 0380309 A1 | 1/1990 |
| EP | 1149562 B1 | 2/2006 |
| EP | 1695677 A2 | 8/2006 |
| EP | 1405603 B1 | 7/2007 |
| EP | 1695677 A3 | 7/2010 |
| EP | 2213261 A1 | 8/2010 |
| EP | 1474047 B1 | 10/2010 |
| EP | 2335653 A1 | 6/2011 |
| EP | 1555962 B1 | 9/2011 |
| EP | 1745764 A3 | 11/2011 |
| EP | 2168506 B1 | 11/2011 |
| EP | 1994914 B1 | 5/2012 |
| EP | 2484315 A1 | 8/2012 |
| EP | 2363098 B1 | 9/2012 |
| EP | 1459686 B1 | 10/2013 |
| EP | 2484315 B1 | 6/2014 |
| WO | 8807356 A1 | 10/1998 |
| WO | 0013133 A1 | 3/2000 |
| WO | 03068078 A1 | 8/2003 |
| WO | 03096953 A2 | 11/2003 |
| WO | 03096953 A3 | 11/2003 |
| WO | 2004001569 A2 | 12/2003 |
| WO | 2004030557 A1 | 4/2004 |
| WO | 2004032806 A1 | 4/2004 |
| WO | 2004069041 A2 | 8/2004 |
| WO | 2004071310 A1 | 8/2004 |
| WO | 2005041822 A2 | 5/2005 |
| WO | 2005048853 A3 | 6/2005 |
| WO | 2005072629 A1 | 8/2005 |
| WO | 2006091423 A2 | 8/2006 |
| WO | 2007016285 A2 | 2/2007 |
| WO | 2007016285 A3 | 2/2007 |
| WO | 2007038776 A2 | 4/2007 |
| WO | 2007038776 A3 | 4/2007 |
| WO | 2008039926 A2 | 4/2008 |
| WO | 2008039926 A3 | 4/2008 |
| WO | 2008069800 A1 | 6/2008 |
| WO | 2011092337 A1 | 8/2011 |
| WO | 2011160008 A1 | 12/2011 |
| WO | 2012064513 A1 | 5/2012 |
| WO | 2012118696 A1 | 9/2012 |
| WO | 2012129566 A2 | 9/2012 |
| WO | 2012129566 A3 | 9/2012 |
| WO | 2012173605 A1 | 12/2012 |
| WO | 2013091085 A1 | 6/2013 |

OTHER PUBLICATIONS

SUPERPATH Trademark Statement of Use with specimens filed on Oct. 10, 2012. Owner Wright Medical Technology, Inc.

SUPERPATH Trademark Application filed with specimens on Apr. 5, 2013. Owner Wright Medical Technology, Inc.

Depuy International Ltd Silent Surgical Product Rational Cat No. 9476-58-001 version 2 updated publication revised date Jul. 2010.

Depuy International Ltd Silent Surgical Technique Cat No. 9476-58-000 version 1 undated publication revised date Nov. 2009.

Google Image Search of Dimensions of femoral neck.

J.R.T. Jeffers, J Latham, P Williams, A Taylor and M.A. Tuke Laser Guided Instrumentation for Acetabular Cup Placement in Hip Arthroplasty Abstract to article J Bone Joint Surg BR 2010 vol. 92-B No. SUPPl 111.

James B. Stiehl, Donald Jacobson and Guilermo Carrera Morphological analysis of the proximal femur using quantitative computed tomography published Aug. 2, 2006 Springer-Verlag.

De Sousa, E.; Fernandes, R.M.P.; Mathias M.B.; Rodrigues, M.R.; Ambram A.J. & Babinski, M.A. Morphometric study of the proxi-

(56) References Cited

OTHER PUBLICATIONS mal femur extremity in Brazilians, Int. J. Morphol., 28(3):835-840, 2010.

* cited by examiner

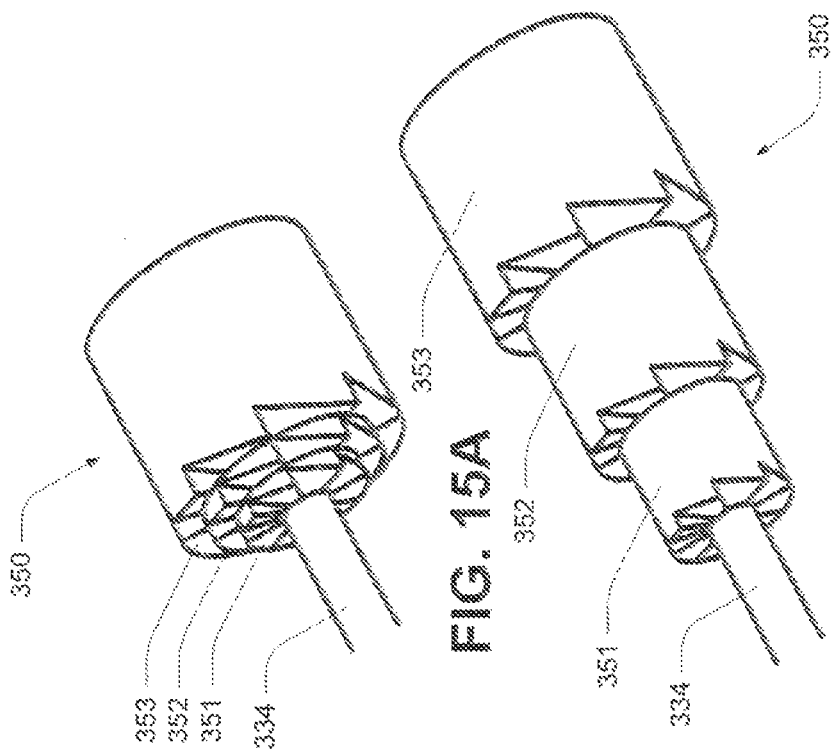
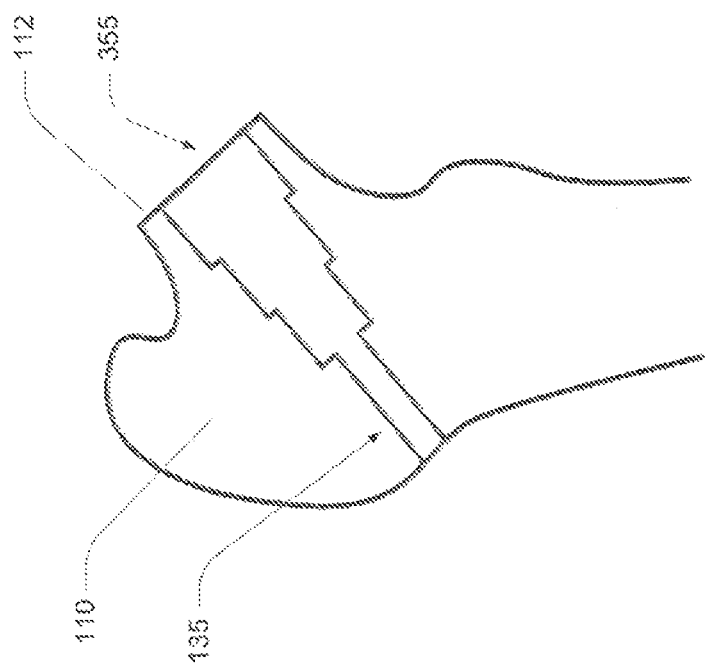

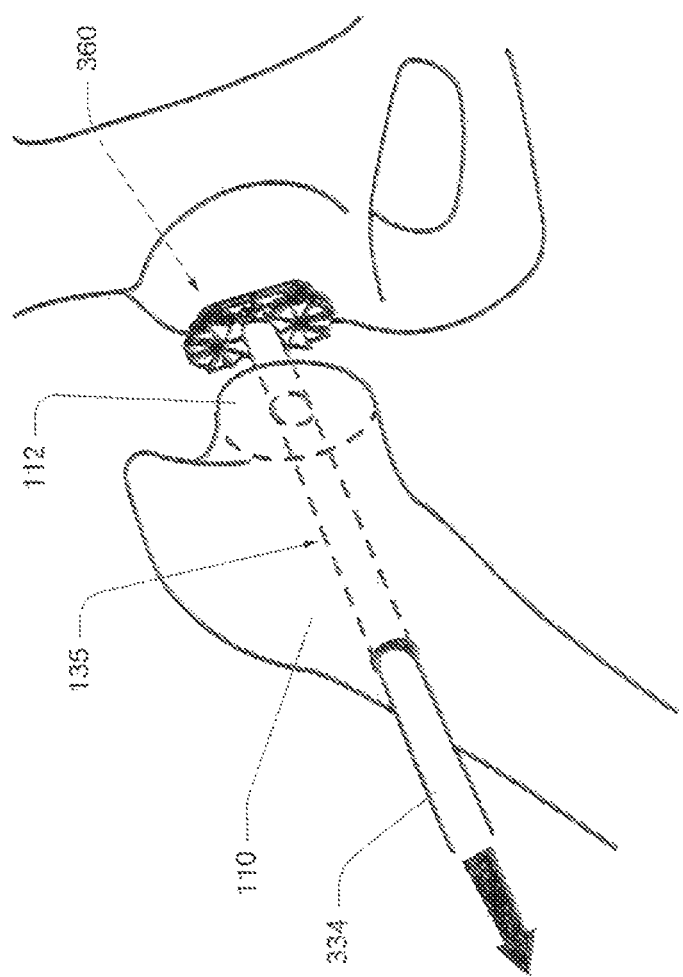

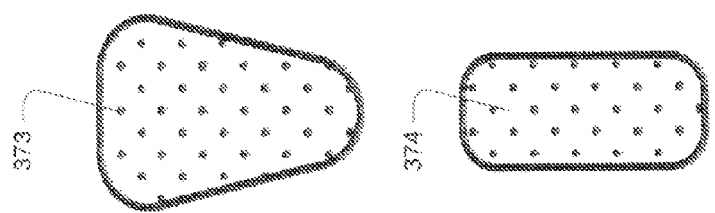
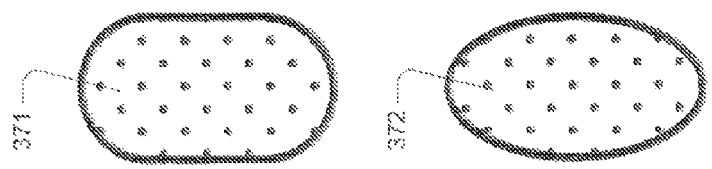
FIG. 17B

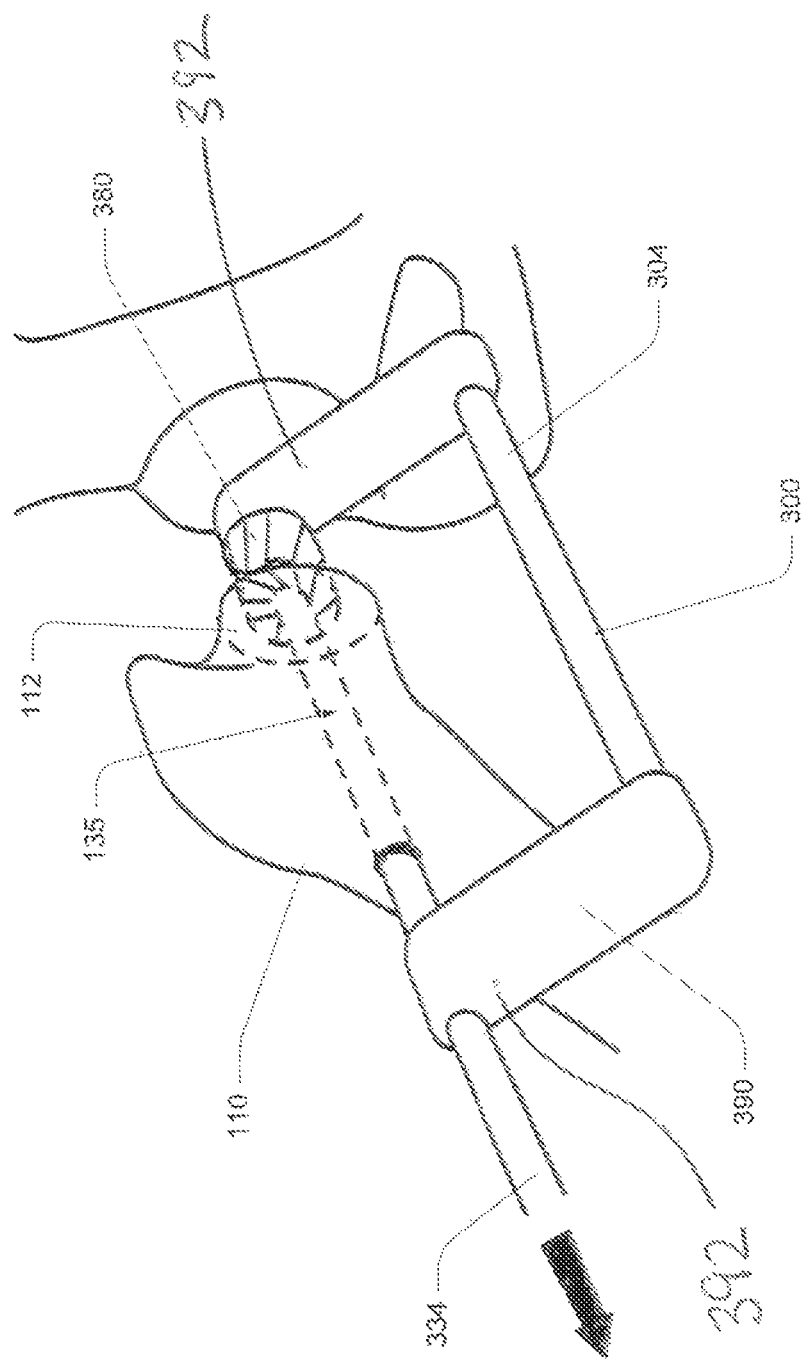

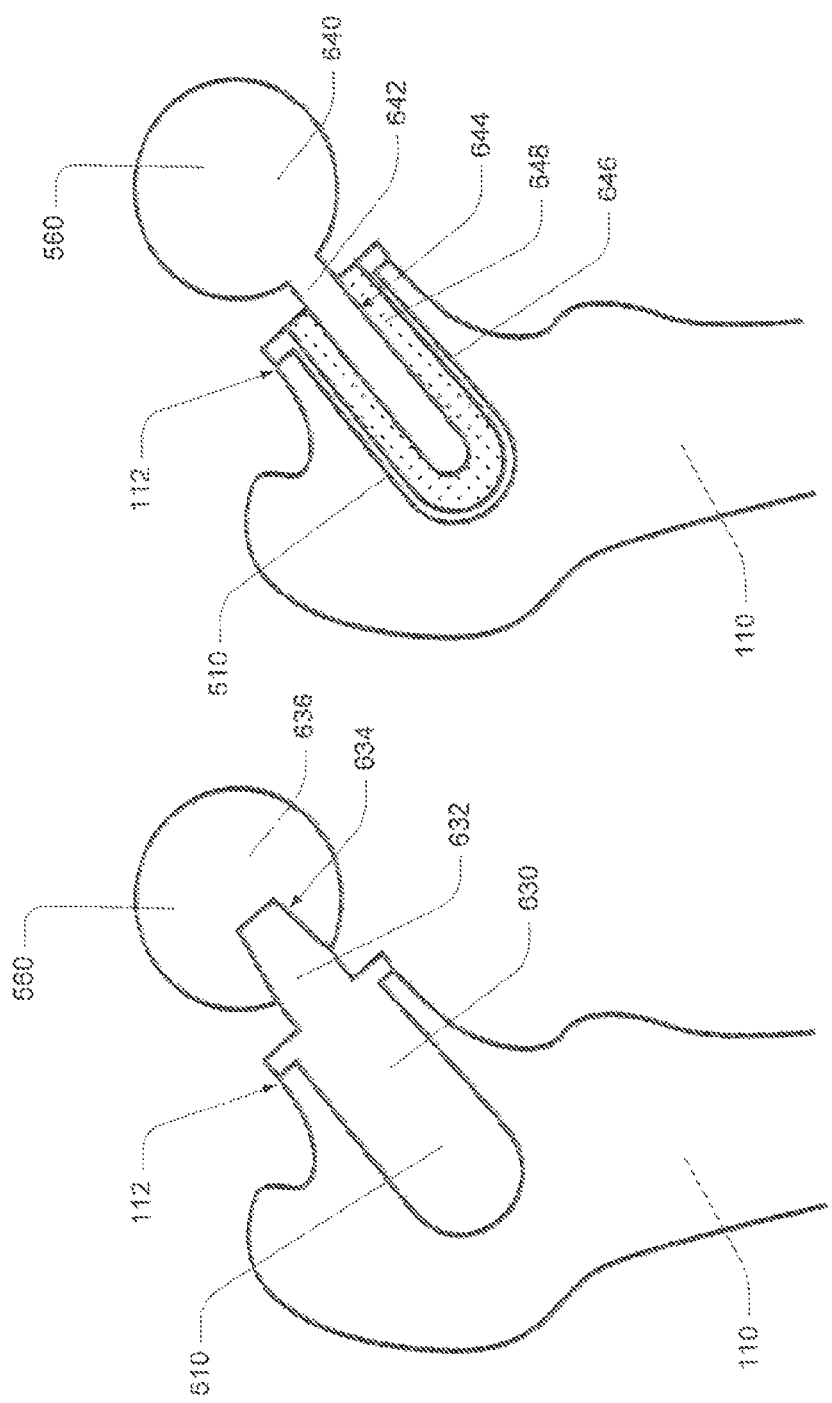

METHOD AND APPARATUS FOR HIP REPLACEMENTS

CROSS-REFERENCE TO RELATED APPLICATIONS

This application claims the benefit of Australian Provisional Application No. 2012903977, filed Sep. 12, 2012, which is hereby incorporated by reference herein in its entirety, including but not limited to those portions that specifically appear hereinafter, the incorporation by reference being made with the following exception: In the event that any portion of the above-referenced provisional application is inconsistent with this application, this application supercedes said above-referenced provisional application.

STATEMENT REGARDING FEDERALLY SPONSORED RESEARCH OR DEVELOPMENT

Not Applicable.

BACKGROUND

1. The Field of the Present Disclosure

The present disclosure relates generally to orthopaedic methods and apparatus, and more particularly, but not necessarily entirely, to methods and apparatus for use in arthroplasty treatments.

2. Description of Related Art

Arthroplasty techniques are varied, but share the same goal of removing the dysfunctional arthritic joint areas and replacing them with materials that preserve joint function. Specifically, hip arthroplasty treatments or procedures are intended to provide a pain-free weight bearing joint whose motion replicates the native hip joint.

Arthroplasty procedures of the hip joint specifically target disease of the femoral head (ball portion) and acetabulum (socket portion). Traditional total hip replacement surgery excises the femoral head and a portion of the femoral neck as well as reaming the acetabulum. Resurfacing-type procedures excise a portion of the femoral head both distally and around the edges as well as reaming the acetabulum. Partial resurfacing procedures typically result in a portion of the femoral head being resected. Substituted in their place are materials that possess durability and function.

Surgical techniques to accomplish arthroplasty goals are typically open techniques, rather than arthroscopic type techniques. Open techniques typically involve a full incision that substantially exposes the hip joint, resulting in significant iatrogenic soft tissue trauma. Arthroscopic techniques used in arthroplasty treatments are typically made from the anterior aspect of the thigh, wherein the two arthroscopic portals are the anterior/mid anterior and antero-lateral. Other portals have also been utilised, including the accessory lateral portal and postero-lateral portal.

Although arthroscopic examination, evaluation, and treatment of the hip and hip region exist, techniques used in hip arthroplasty treatments typically require substantial dislocation of the hip joint, with associated soft tissue dissection, for enabling the necessary tools/devices to be used in situ and to install any required prosthesis.

For example, U.S. Patent Publication No. 2003/0130741, published Jul. 10, 2003 to McMinn, discloses a method of resurfacing a hip joint using a first incision made at the patient's hip joint, and a second incision made at the outer side of the patient's thigh. In particular, McMinn first teaches that a guide wire is installed through the second incision up and into the femoral head and neck. Following insertion of the guide wire, McMinn next teaches that the femoral head is dislocated from the acetabulum. With the femoral head dislocated, the guide wire is then over-drilled to produce a canal up the femur and exiting the zenith of the femoral head. Using a drive rod inserted through the second incision and up the femoral canal, the periphery of the femoral head is resected using a sleeve cutter inserted through the first incision. A sleeve resection guide inserted through the first incision is then utilized to resect an appropriate amount of the zenith of the femoral head using a cutting blade. A chamfer cutter, inserted through the first incision, is then utilized to cut the femoral head to provide a chamfer thereon. Once the femoral head has been prepared, an acetabular reamer is inserted through the first incision and connected to the drive rod. The acetabular reamer can then be utilized to ream the acetabulum. McMinn then teaches the installation of an acetabular cup and femoral component are implanted.

By way of another example, U.S. Pat. No. 7,695,474, granted Apr. 13, 2010 to Crofford, discloses a method of resurfacing a hip joint using a femoral neck fixation prosthesis. Crofford discloses that an artificial femoral head is attached to a fixation prosthesis, which extends coaxially through a femoral canal formed in the femoral neck, into the femur, and is then attached to the opposite lateral wall of the femur. Crofford further teaches that the implantation of the femoral neck fixation prosthesis is accomplished by resecting the femoral head, reaming at least one passage in the femoral neck, reaming the acetabulum, and implanting the femoral neck fixation prosthesis into the reamed passage. Crofford further discloses that access to the femoral head and neck is accomplished by dislocating the femoral head from the acetabulum and rotating the leg of the patient to expose the head and neck.

One drawback of the method taught in McMinn and Crofford is the explicit requirement that the hip be dislocated during the procedure in order to expose the femoral head and neck. In particular, while hip dislocation during hip arthroplasty surgery is beneficial to expose the femoral head and neck, this procedure may cause significant soft tissue damage that may prolong patient recovery time and increase the probability of postoperative complications. Accordingly, there is a need in the art for improved methods and apparatus for arthroplasty treatments using arthroscopic techniques which lower the risk of iatrogenic injury, postoperative complications, and provide improved means for performing arthroscopic hip treatments and procedures.

The prior art is thus characterized by several disadvantages that are addressed by the present disclosure. The present disclosure minimizes, and in some aspects eliminates, the above-mentioned failures, and other problems, by utilizing the methods and structural features described herein.

The features and advantages of the present disclosure will be set forth in the description which follows, and in part will be apparent from the description, or may be learned by the practice of the present disclosure without undue experimentation. The features and advantages of the present disclosure may be realized and obtained by means of the instruments and combinations particularly pointed out in the appended claims.

BRIEF DESCRIPTION OF THE DRAWINGS

The features and advantages of the disclosure will become apparent from a consideration of the subsequent detailed description presented in connection with the accompanying drawings in which:

FIG. 9A is a side view of the femoral surface reamer of FIG. 9;

FIG. 15A is a schematic view of an embodiment femoral reamer device, shown in a closed configuration;

FIG. 15B is a schematic view of the embodiment femoral reamer device of FIG. 15A, shown in an extended configuration;

FIG. 15C is a schematic view of a femur, having a femoral cavity created by the embodiment femoral reamer device of FIG. 15B;

FIG. 16A is a schematic view of the layout of FIG. 1, showing an embodiment femoral reamer device coupled to an embodiment femoral elongate element;

FIG. 17B shows four alternative profile configurations for the embodiment femoral reamer device of FIG. 17A;

FIG. 18 is a schematic view of the layout of FIG. 1, showing an embodiment femoral reamer device coupled to an embodiment outrigger device;

FIG. 23C is a schematic view of a femur—showing installation of an embodiment femoral stem element, femoral neck component and femoral head component;

FIG. 23D is a schematic view of a femur—showing installation of an embodiment femoral stem element, femoral neck component and femoral head component;

DETAILED DESCRIPTION

Figure 1:
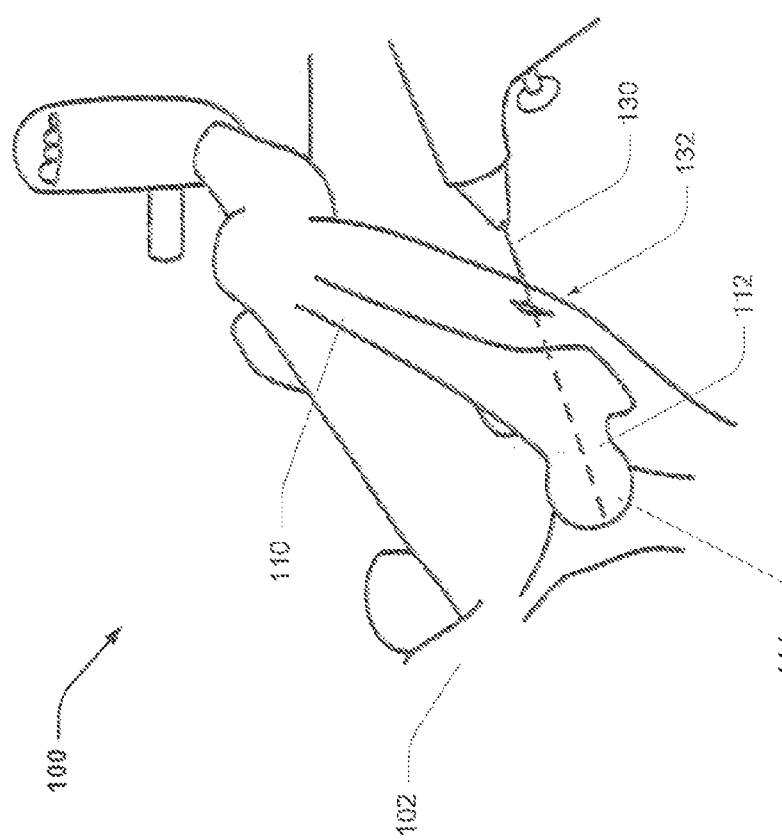
FIG. 1 is a schematic view of an embodiment hemipelvis pre-operative cross sectional layout, showing insertion of an embodiment femoral guide.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

In describing and claiming the present disclosure, the following terminology will be used in accordance with the definitions set out below. It must be noted that, as used in this specification and the appended claims, the singular forms "a," "an," and "the" include plural referents unless the context clearly dictates otherwise. As used herein, the terms "comprising," "including," "containing," "characterized by," and grammatical equivalents thereof are inclusive or open-ended terms that do not exclude additional, unrecited elements or method steps.

The present disclosure includes devices, apparatus and methods for arthroscopic examination and treatment, particularly for medical procedures in and near a hip joint of a patient. The devices may be disposable, single use, multi use or reusable devices. The devices, apparatus and methods of the present disclosure are useful for the partial or complete arthroplasty of the hip joint via arthroscopic and/or computer navigated applications. Embodiments of the devices, apparatus and methods of the present disclosure are effective to assist an operating surgeon in hip joint surgery.

Hip replacement generally involves insertion of a femoral component into the femur to which is fixed a prosthetic head element, and an acetabular component (typically including a liner element of polyethylene, ceramic or metal) that is located into the prepared acetabulum. This procedure typically requires excision or resurfacing of the femoral head for installation of a prosthetic femoral component.

The femoral component can involve a stem element that extends down inside the femoral canal (typically after preparation of the canal with one or more bone broaches). The femoral component can comprise any one of a plurality of designs or shapes. The femoral component can be located in the femoral shaft and has a neck portion for engaging a prosthetic head element. By way of example only, the femoral component can have curved shape for following the contour of the femoral neck or can be inserted straight within the femoral neck.

Previously known techniques and apparatus for performing hip replacements require substantial soft tissue dissection and dislocation of the hip joint to obtain/maintain adequate exposure. Preparation of the femur is typically performed, with reference to the femoral neck and head, in the direction from proximal to distal (cephalad-to-caudal/head-to-tail), such that the femoral neck can be directly visualised in all of these procedures. By way of example, preparation of the femur in these procedures can involve: dissection and retraction of the soft tissues to expose the femoral neck; then cutting the femoral neck with a saw under visual supervision; pushing reamers, or hitting bone broaches, down into the femoral canal in a direction from proximal to distal. Preparation of the acetabulum is typically performed after moving (retracting) the femur out of the way, and under direct vision through the incision, by reaming the surface through the incision.

With reference to the orientation and configuration of the patent hip and apparatus, it would be understood that: (i) the proximal direction or portion is direction or portion toward the femoral head and acetabulum, substantially along the axis of the neck portion femoral shaft, while the distal direction or portion is an opposing orientation; and (ii) the anterior direction or portion is forward facing direction or portion, with respect to the patient, while the anterior direction or portion is an opposing orientation.

In an embodiment, the method and apparatus disclosed herewith teaches an alternative retrograde (being opposite to typical hip replacement techniques) femur preparation (or humerus preparation), wherein preparation devices are pulled down onto the femur rather than pushing the preparation device down from a proximal cut end. A reamer or broach is pulled down from proximal to distal through a hole in the lateral aspect of the femur—thereby not requiring the femoral neck to be under direct vision, and allowing the hip to be maintained in a resting position.

In an embodiment, the method and apparatus disclosed herewith teaches an alternative acetabulum preparation, wherein once the femoral head is excised, acetabular bone is prepared with a reamer (or a burr) device manipulated (or controlled) through a hole in the lateral aspect of the femur—thereby requiring the femoral neck to be appropriately aligned with the acetabulum (and not retracted). It would be known that routine acetabular reaming requires the femur to be retracted away from the acetabulum to provide adequate exposure.

It will be appreciated that the present disclosure prepares the femur and acetabulum with minimal soft tissue dissection and without dislocation—while maintaining the hip in natural (ideal) position—and thereby minimising trauma to the tissues and minimising the risk of dislocation. While is it anticipated that the patient will typically placed supine (on their back), the procedure could also be performed on a patent in a lateral position.

Referring to FIG. 1, an embodiment hemipelvis pre-operative cross-sectional layout 100 of an arthroscopically assisted arthroplasty of a patient 102, includes a femur 110 having a femoral neck 112 and a femoral head 114, an acetabulum 120. A femoral guide wire/pin 130 is inserted in the femoral neck, typically for a planned femoral osteotomy cut at 90 degrees to the femoral guide 130. Access for inserting the femoral guide 130 is through a lateral incision 132 at the outer side of the thigh. The femoral passage or guide 130 can be drilled through the lateral cortex of the femur along the center of the femoral neck 112 on the antero-posterior and lateral views. The femoral passage or guide 130 can be directed using an external alignment jig, a navigation system, or x-ray control system, image intensifier system, or any other imaging or navigation modality.

Through the lateral incision 132, the femoral guide 130 can be inserted into the lateral aspect of the femur 110 and up into the femoral head and neck, with the desired position obtained using an external alignment jig, a navigation system, a computer navigation system, an x-ray control system, image intensifier system or any other imaging modality. The dimension of the femoral guide 130 is typically 1 mm to about 5 mm in diameter, for example 2.5 mm. Following insertion of the guide-wire, the femoral head need not be dislocated from the acetabulum. It would be appreciated that a traction table 140 or other fixation means can be may be used to maintain the relative orientation of the femur and patient.

Figure 2:
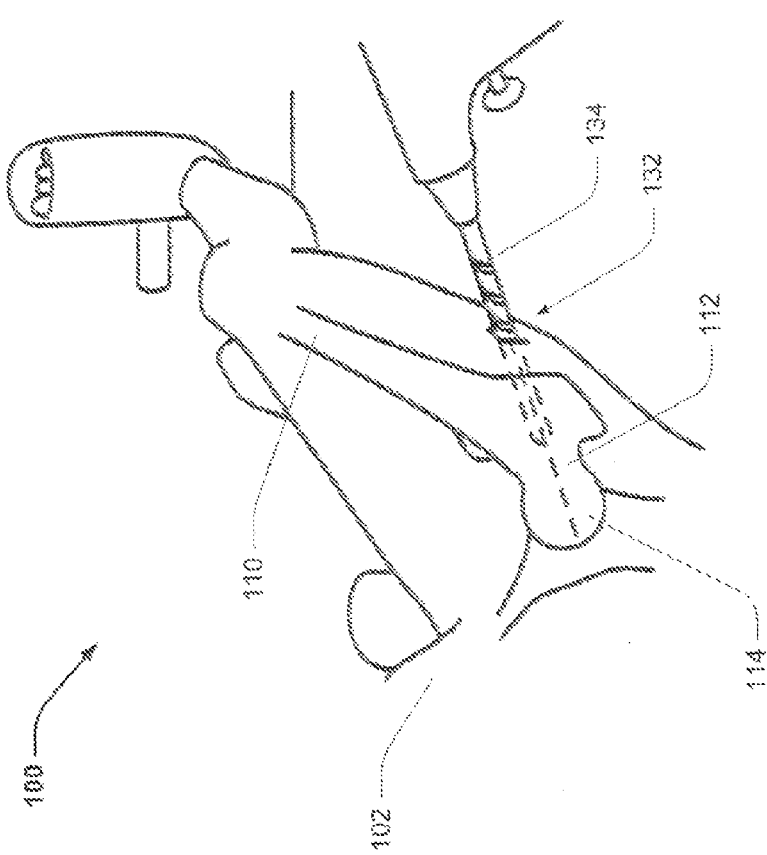
FIG. 2 is a schematic view of the layout of FIG. 1, showing insertion of an embodiment femoral elongate element.

Referring to FIG. 2, a femoral elongate element (or femoral rod) 134 can be located (reamed) over the femoral guide 130 to a selected distance using a measurement system on the element 134, image/navigation modality or measurement modality. (The femoral elongate element 134 may include a hollow passageway for receiving the femoral guide 130.) The femoral elongate element 134 can be located in or define a femoral passage 135. The dimension for the femoral elongate element (or femoral rod) 134, by way of example only, can be 6 mm to 10 mm in external diameter. In an embodiment, the femoral elongate element 134 can be drilled all the way into the joint, through the zenith of the head 114 using a drill. The depth distances can be visualized with markings on the element 134 or using a navigation method.

Figure 3:
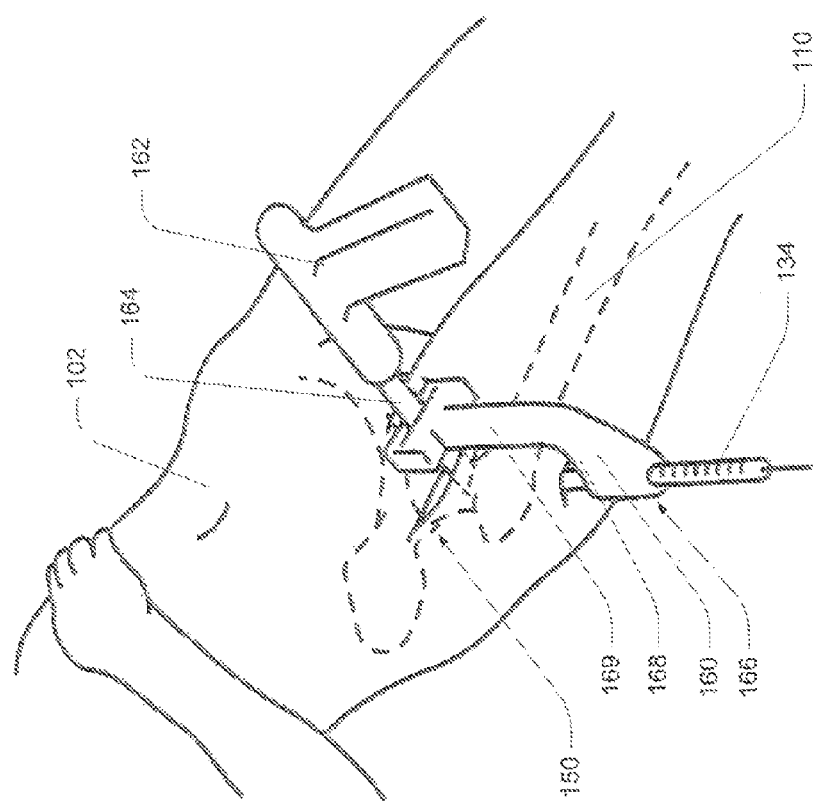
FIG. 3 is a schematic view of the layout of FIG. 1, showing an embodiment outrigger device for excising the femoral head.

Referring to FIG. 3, an anterior incision 150 exposes the anterior portion of the femoral neck. While this is typically performed through an anterior approach, it would be appreciated that any approach could be used. The incision only has to be large enough to insert the preparation devices and the final components. By way of example only, the anterior incision 150 can be about 5 cm. It will be appreciated that, by way of example, the hip capsule can be cut in a T-fashion to expose the femoral neck.

An outrigger device 160 may be fixedly coupled to the femoral elongate element (or femoral rod) 134 for enabling cutting of the femoral neck 112 at the femoral head-neck junction through the anterior incision 150. Removal of the femoral head 114 can be typically made with an excise device (for example a saw device or a burr device) 162. Removal of the femoral head may leave a neck surface. In an embodiment, the excise device 162 can be an expandable cutter device that is locatable inside the femoral neck 112 for cutting the neck 112 from inside out.

Removal of the femoral head 114 can be typically achieved by cutting of the femoral neck 112. In an embodiment, the femoral head 114 could be entirely removed with a burr device. The outrigger device 160 and an appropriate jig 164 are used to maintain the excise device in the correct location and orientation. It will be appreciated that the femoral osteotomy cut can with reference degrees to the femoral guide and femoral elongate element (or femoral rod) as these have a fixed orientation to the femoral neck 112, using the outrigger device 160 and an appropriate jig 164 to maintain the excise device 162 in the correct location and orientation. The femoral head 114 may then be removed.

It would be further appreciated that the outrigger device arm can be height adjustable (not shown) to accommodate patients of difference size. In an embodiment, the outrigger device 160 can be slotted onto (or sleeved over) the femoral elongate element 134 (or femoral rod) extending from the lateral aspect of the femur 110. By way of example only, the outrigger device 160 can include an upwardly extending portion 168 and laterally extending portion 169. Moving the outrigger device 160 along the axis of the femoral elongate element 134 can be achieved by sliding the device 160 along the femoral elongate element 134 (or femoral rod) (or a separate sliding mechanism joined/associated with the upwardly extending portion and/or laterally extending portion).

In this embodiment the outrigger portions are substantially perpendicular to each other. It would be appreciated that the outrigger portions can have a movable junction (for example, a sliding and locking junction or a ratchet locking junction) for accommodating different patient size anatomies. The jig 164 can have a guide portion for the femoral neck cut, which can preferably be adjusted to reduce cut error by locating the guide closer (or proximal) to the patient skin (for example, including an adjustment mechanism for moving the jig and guide in the plane of the anterior incision and femoral neck cut).

In an embodiment, by way of example only, the outrigger device 160 includes an outreaching, curved arm portion having an aperture at one end for receiving a guide rod, or the femoral elongate element 134, and being slidably movable along the rod. The other end of the arm comprises a cutting guide that is adapted to receive a saw blade. Typically the cutting guide is an elongate slot that is orientated perpendicular to the guide rod or the femoral elongate element 134 such that the saw blade is directed to cut the femoral neck perpendicular to the rod. By using an outrigger arm having the cutting guide externally fixed to a rod and located proximal to the femoral neck 112, the femoral neck 112 can be cut through a small incision.

By having a guide aperture of the outrigger arm slidably engaged to the rod or the femoral elongate element 134, the relative location of the cutting guide can be indicated or measured. This allows the outrigger arm to be moved along the rod or the femoral elongate element 134, such that portion of bone to be retained (or removed) is measurable. Alternatively, a gauge element can be slidably engaged to the rod or the femoral elongate element 134 to first measure and used to measure the amount of bone to be removed/retained and indicate the required location for the outrigger arm.

Figure 4:
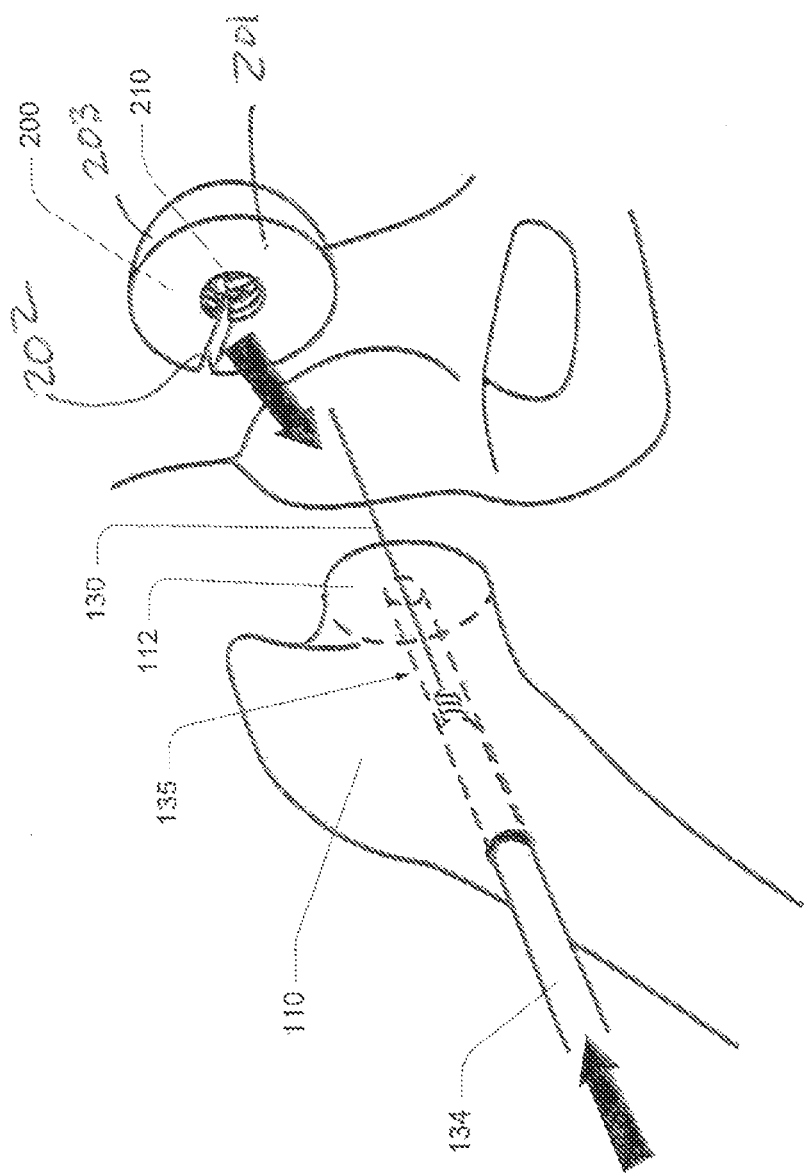
FIG. 4 is a schematic view of the layout of FIG. 1, showing an embodiment acetabulum guide device.

Referring to FIG. 4, the femoral guide wire 130 (or femoral guide pin) located in the femoral neck 112 can be guided into the joint space. A plastic semi-spherical acetabulum guide device 200 the same size or slightly smaller than the internal diameter of the acetabulum can be inserted over this guide wire 130 for example through a slot 202 or hole. In particular, the slot 202 may extend from a femoral side 201 of the device 200 to an apex of the acetabulum side 203 of the device 200. Further, the slot 202 may extend radially inward from a perimeter of the femoral side 201 and intersect with a female threaded bore 210 formed along a central axis of the device 200. The slot 202 may be configured and dimensioned to receive the guide wire 130 such that the guide wire 130 may be utilized to orient the device 200 along a central axis of the femoral passage 135.

As mentioned, the device 200 may include the female threaded bore 210 for receiving a male threaded end of a femoral elongate element (or femoral rod) 134. It will be appreciated that the use of the femoral guide wire 130 or pin may not be required, typically depending on the size of the patient and the incision.

In an embodiment, it will be appreciated that the femoral guide wire 130 can be placed slightly into the acetabular bone for added stabilisation. Alternatively, if using computer navigation, the position of the leg could be recorded and then reproduced for acetabular reaming, thereby reducing the requirement for using a traction table.

Figure 5:
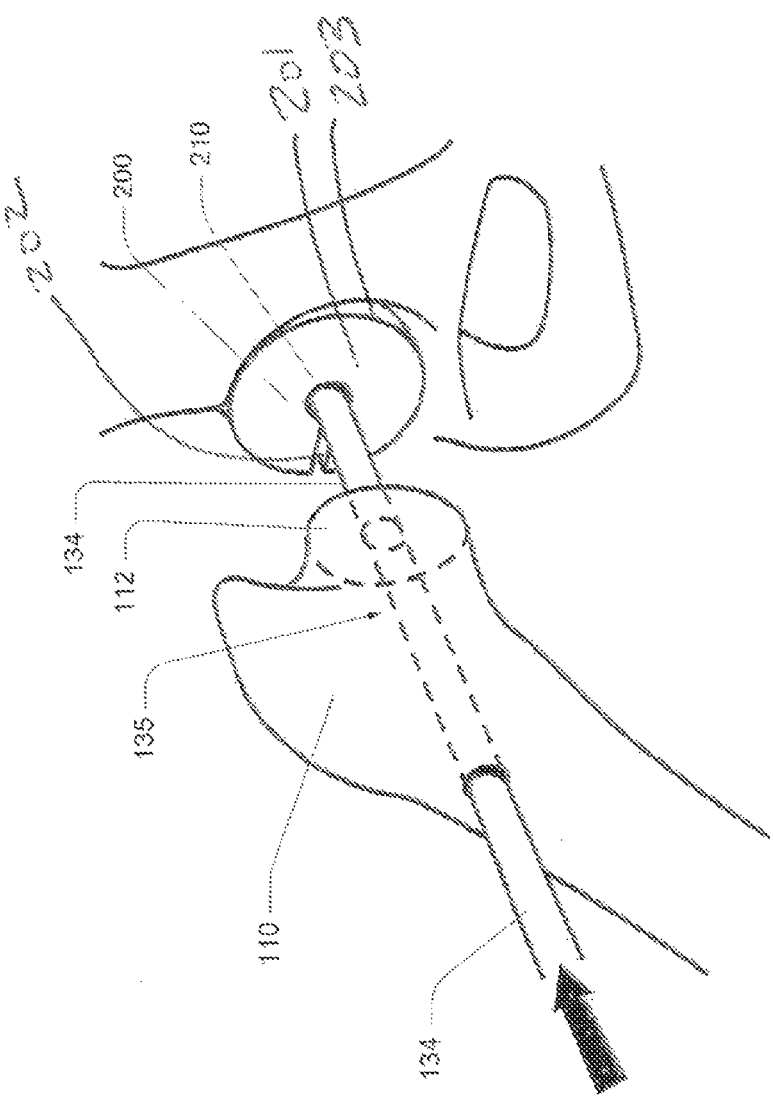
FIG. 5 is a schematic view of the layout of FIG. 1, showing an embodiment acetabulum guide device coupled to an embodiment femoral elongate element.

Referring to FIG. 5, a femoral elongate element (or femoral rod) 134 can be advanced, to engage the semi-spherical acetabulum guide 200. The acetabulum guide 200 can be manufactured in plastics (or other suitable material) for use in surgery. For example, the femoral elongate element (or femoral rod) 134 can be releasably engaged to the acetabulum guide 200, to a predetermined depth (for example 5 mm to 10 mm). For example, the femoral elongate element (or femoral rod) 134 can be threadedly engaged to a central threaded aperture 210 of the acetabulum guide 200. This engagement can be used to align the femur neck 112 (having an orientation along the axis of the femoral elongate element (or femoral rod) 134 and the acetabulum 120 to a preferred (or optimal) position for subsequent acetabular reaming. It will be appreciated that, with the femoral elongate element (or femoral rod) 134 in place, the leg can be manipulated into any position, and the acetabulum guide 200 located in a preferred location within the acetabulum, for subsequent acetabular reaming.

It would be appreciated that this manipulation can be conducted using arthroscopic assistance to observe the configuration of the acetabulum guide 200, such that it is best located in relation to the normal acetabular rim. The acetabulum guide 200 would typically or preferably sit at the edge of the normal acetabulum after osteophytes have been removed. Osteophytes can be removed with a burr by direct visualisation or more easily arthroscopically assisted.

In an embodiment, once the preferred position of the acetabulum guide 200 is found the femur or leg is restrained by any suitable technique in this configuration using the table 140. The femoral elongate element (or femoral rod) 134 can be partially retracted and the acetabulum guide 200 removed. It will be appreciated that the patient leg would be preferably, but not necessarily, attached to a fracture table to allow manipulation into the desired position and placed in traction.

Figure 6:
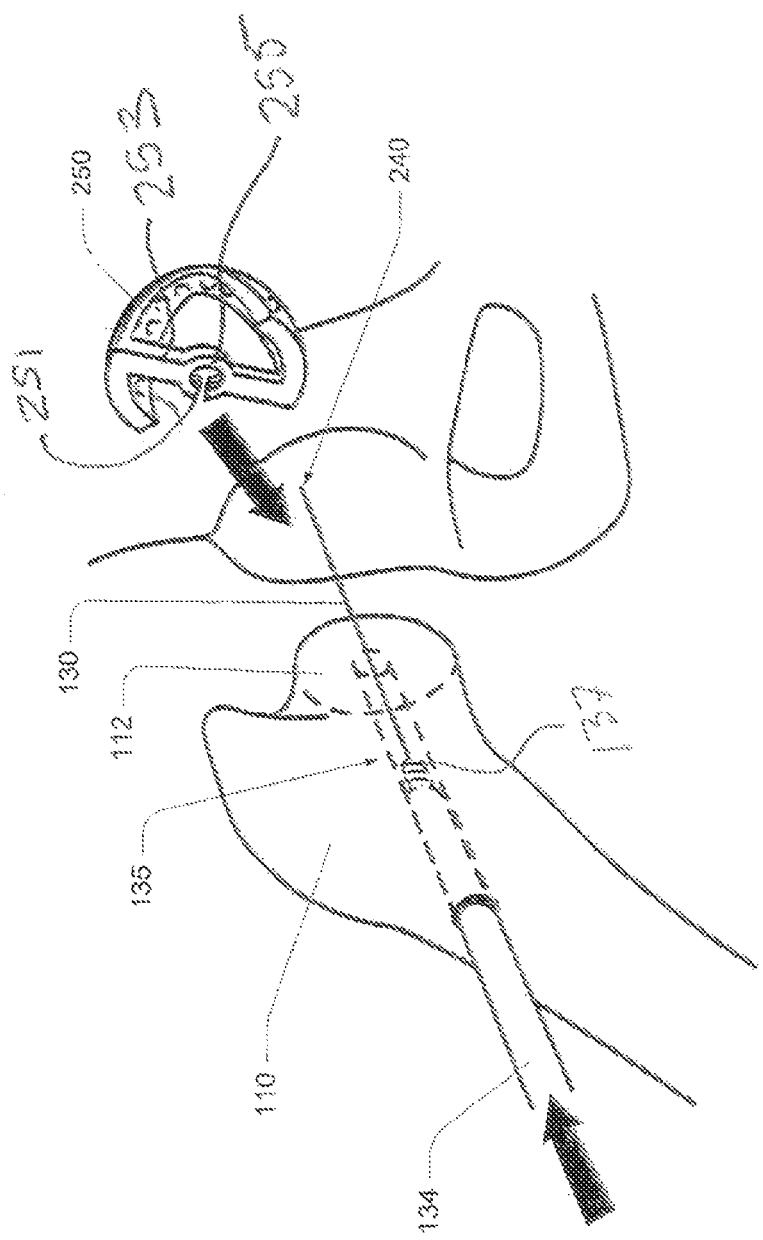
FIG. 6 is a schematic view of the layout of FIG. 1, showing an embodiment acetabulum reamer device.

Referring to FIG. 6, in an example embodiment, the femoral guide 130 can be embedded (or drilled) into the acetabular bone at 240 to improve stability of the femur/leg and assist positioning of an acetabular reamer 250. By way of example only, the femoral guide 130 can be embedded a few millimeters into the acetabular bone 240. In an embodiment, the acetabular reamer 250 can then be located within the hip joint space, fitting over the femoral guide 130 if required, with the assistance of a guide slot 251. In particular, the acetabular reamer 250 may include a femoral side 253 (distal side or bone side, which is opposite the proximal or socket side). Disposed along an axis of the acetabular reamer 250 on the femoral side 253 may be a female threaded bore 255. The guide slot 251 may extend from a perimeter of the femoral side and into the female threaded bore 255 such that the guide wire 130 may be laterally slid into the bore 255. The guide slot 251 may extend to an apex of the reamer 255. With the guide wire 130 installed in the bore 255, a threaded end of the femoral elongate element 134 may be slid up the guide wire 130 and coupled to the bore 255 of the acetabular reamer 255.

The femoral elongate element (or femoral rod) 134 can then be releasably engaged to the acetabulum reamer 250. The femoral elongate element (or femoral rod) 134 entering from the lateral femoral cortex can be threadedly engaged to the acetabulum reamer 250 thereby providing the preferred orientation and location of the acetabulum reamer. It will be appreciated that the femoral guide 200 may not be required.

It will be appreciated that this technique can enable anatomical placement of the acetabular component that substantially mimics the patient anatomy. Other anatomical landmarks can be viewed arthroscopically, including the inferior transverse ligament or labral edge.

Figure 7:
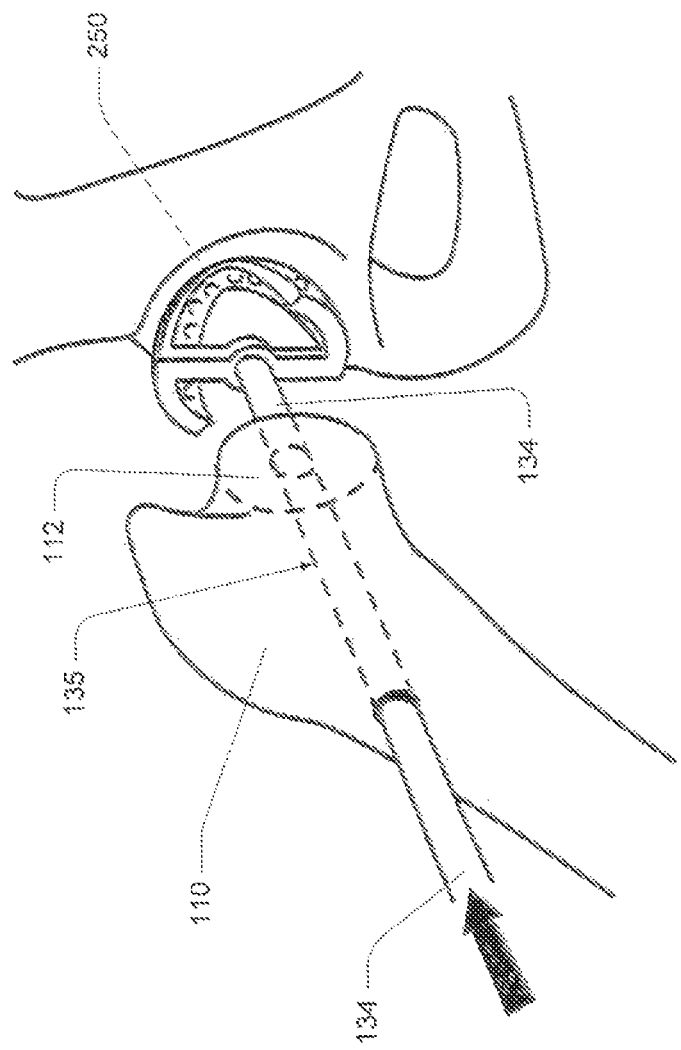
FIG. 7 is a schematic view of the layout of FIG. 1, showing an embodiment acetabulum reamer device coupled to an embodiment femoral elongate element.
Figure 8:
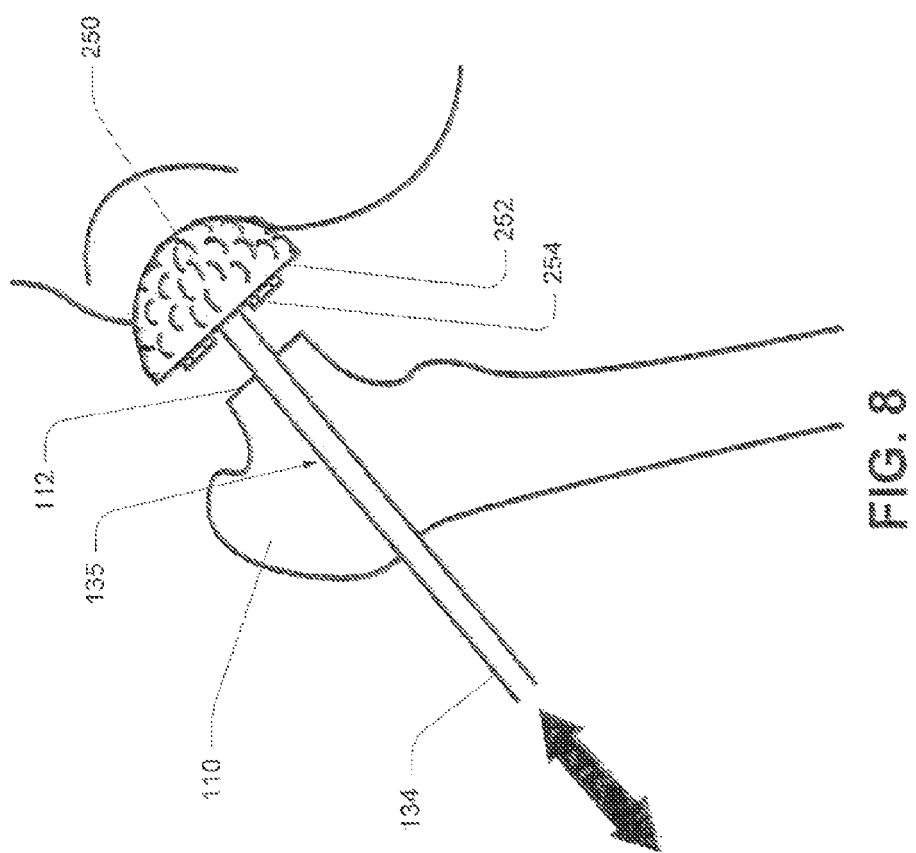
FIG. 8 is a schematic view of the layout of FIG. 1, showing an embodiment acetabulum reamer device coupled to an embodiment femoral elongate element.

Referring to FIG. 7, the acetabular reamer 250 is used to ream or reconfigure the acetabulum. The femoral elongate element (or femoral rod) 134 is moved proximally to engage the acetabular reamer 250 with the acetabulum as best shown in FIG. 8. The acetabular reamer 250 is rotated by rotating the femoral elongate element (or femoral rod) 134 coupled to the acetabulum reamer 250, rotating an outer sleeve coupled to the acetabulum reamer 250 or rotating an inner shaft or sleeve coupled to the acetabulum reamer 250. The femoral elongate element (or femoral rod) 134 is then partially retracted (or withdrawn) and the acetabular reamer 250 removed.

It will be appreciated that the acetabular reamer 250 is preferably of a minimally invasive configuration (less than a hemisphere) for allowing insertion through the relatively small incision. It would be further appreciated that a variety of acetabulum reamer configurations and combinations can be used, including: a single acetabulum reamer, multiple acetabulum reamers, or single expandable acetabulum reamer.

Figure 9:
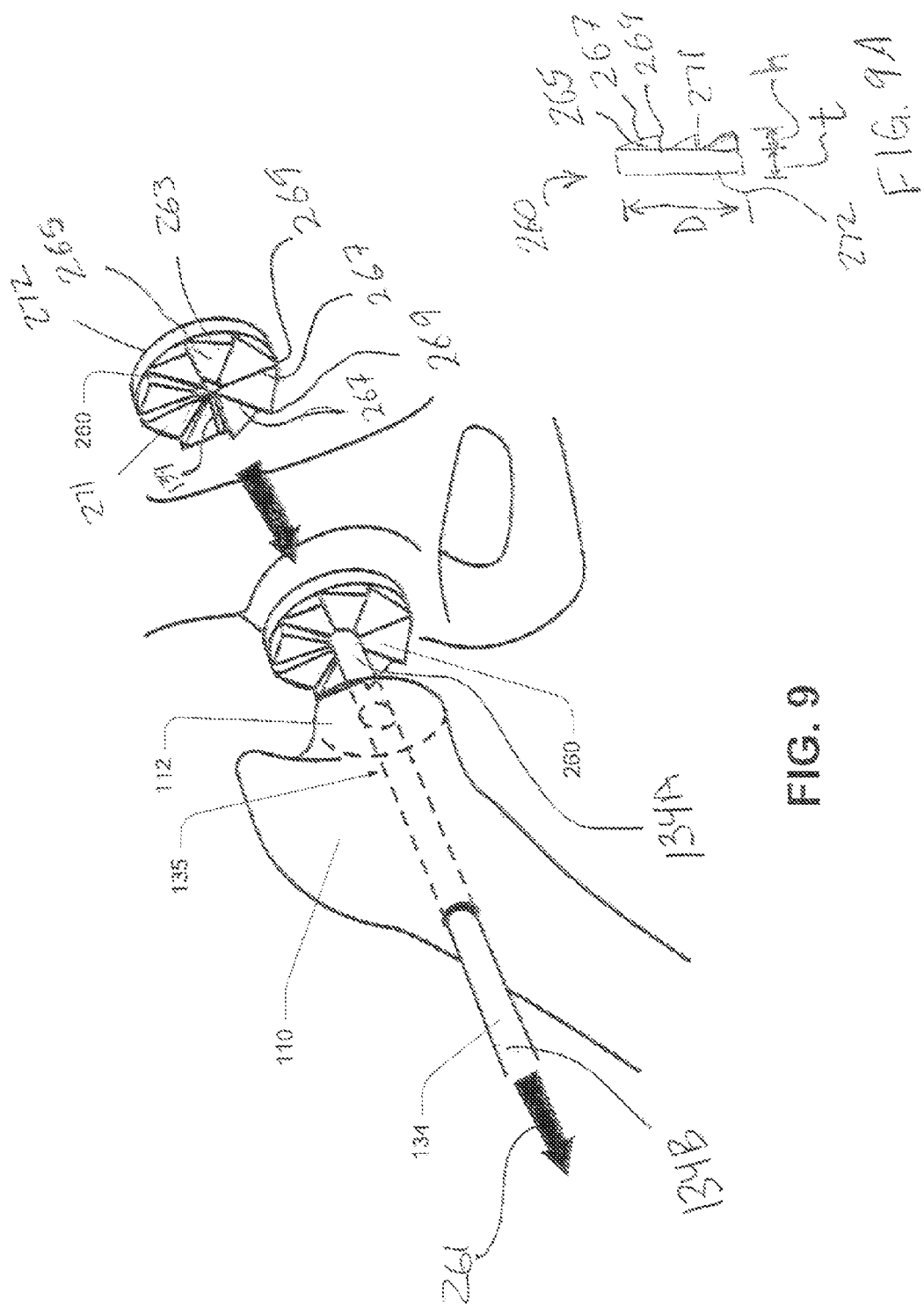
FIG. 9 is a schematic view of the layout of FIG. 1, showing an embodiment femoral surface reamer device coupled to an embodiment femoral elongate element.

Referring to FIG. 9, the femoral elongate element (or femoral rod) 134 can be releasably engaged to a femoral surface reamer 260 for surface treating (or "cleaning up") the neck cut, thereby making the surface substantially perpendicular to the femoral neck axis, as indicated by the femoral elongate element (or femoral rod) 134 or femoral guide 130. The reamer 260 may include an abrading surface 263 having a plurality of surfacing elements 265, such as teeth, burrs, grit, protrusions, for resurfacing a resecting femoral neck. Each surfacing element 265 may include an abrading edge 267, and also may include an abrading tip 269. The abrading edges 267 may collectively be positioned to reside common to a single plane. The abrading tips 269 may collectively be positioned to reside common to a single plane. In an embodiment, the abrading surface 263 may be substantially planar. In an embodiment, the abrading surface 263 is formed on the distal side of the reamer 260. It will be appreciated that the reamer 260 may be considered a surface preparation device for preparing a cut surface of a bone.

Referring now to FIGS. 9 and 9A, in an embodiment, the reamer 260 may be disc shaped and may define a diameter, D, for the abrading surface 263. The reamer 260 may further include a distal side 271 and a proximal side 272. A thickness, t, may be defined between the distal side 271 and the proximal side 272. In an embodiment, the thickness, t, between the distal side 271 and the proximal side 272 (or the edges 269 of the abrading surface 263 and the backside) may be between about 5 to 10 millimeters. Alternatively, in an embodiment a thickness, t, may be 2 to 10 millimeters, and may therefore also be between 2 to 4 millimeters. In an embodiment, the diameter, D, may be between about 20 to 40 millimeters. In an embodiment, a ratio of the thickness to the diameter (t/D) may be between 0.05 and 0.5, and may therefore constitute any thickness between or including those numbers, including 0.125. In an embodiment, a thickness between the proximal side 272 and tips 269 of the abrading surface 263 may be about 4 to 10 millimeters. In an embodiment, a height, h, of the abrading surface 263 extends from the distal surface 271 to the tips 269, and may be 2 to 3 millimeters.

The femoral elongate element (or femoral rod) 134 can be removably attached to the femoral surface reamer 260, for example, by being threadedly engaged to the femoral surface reamer 260 by a coupler. In an embodiment, the coupler may include a male threaded end (137 in FIG. 6) of the femoral elongate element 134 and a female threaded bore 139 in the femoral surface reamer 260. It will be appreciated that the coupler may include any mechanism for joining the element 134 and reamer 260. Alternatively, the femoral elongate element 134 may be fixedly attached to the femoral surface reamer 260.

In particular, the femoral surface reamer 260 may be moved in the medial-to-lateral direction as shown by the arrow marked with the reference numeral 261. It will be appreciated that a proximal end 134A of the femoral elongate element 134 is the end of the element 134 closest to the acetabulum and the distal end 134B of the element 134 is the end furthest from the acetabulum and may extend from an incision in the outer side of the thigh of the patient such that it is accessible to the surgeon. In addition, while the reamer 260 is being moved in the medial-to-lateral direction, the femoral surfacing reamer 260 may rotated about a longitudinal axis of the femoral elongate element 134. In an embodiment, the reamer 260 is rotated by hand or by connecting a surgical drill to the femoral elongate element 134.

Figure 10:
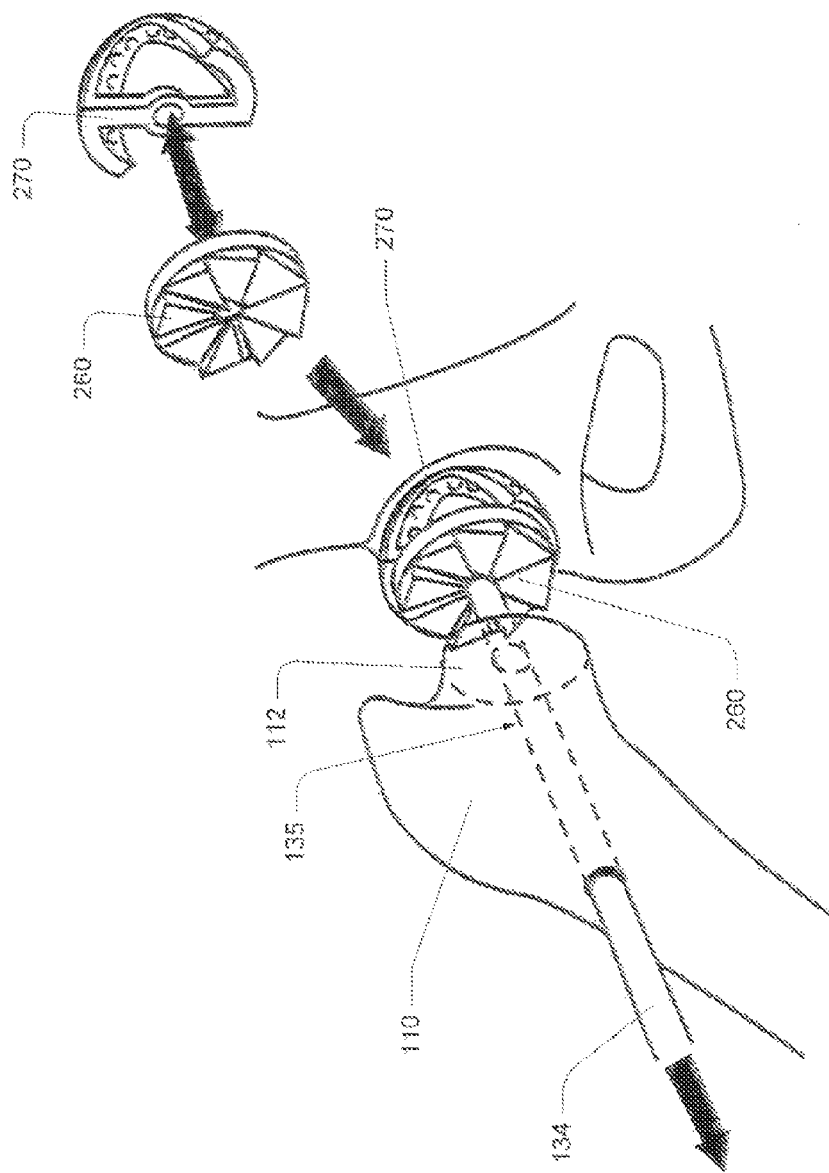
FIG. 10 is a schematic view of the layout of FIG. 1, showing both an embodiment acetabulum reamer device and an embodiment femoral surface reamer device coupled to a femoral elongate element.

In an embodiment, the femoral surface reamer 260 may be coupled to the femoral side 270 of the acetabular reamer 250 (for example by way of threaded engagement)—as best shown in FIG. 10. Thus, it will be appreciated that the acetabular reamer 250 and the femoral surface reamer 260 may be modular. In an embodiment, the acetabular reamer 250 and the femoral surface reamer 260 may be coupled using a threadable engagement. In an embodiment, the acetabular reamer 250 and the femoral surface reamer 260 may be a unitary device.

In an embodiment, a femoral side 270 of the acetabular reamer 250 may be adapted for use for surface treating (or "cleaning up") the neck cut, thereby making the surface perpendicular to the femoral neck axis—as best shown in FIG. 8. By way of example only, an embodiment acetabular reamer 250 can comprise a femoral side surface 252 having cutting teeth 254. It would be appreciated that, because the femoral neck 112 is smaller than the acetabulum, the cutting teeth 254 would typically not be required to extend to the periphery of the acetabular reamer 250.

Figure 11:
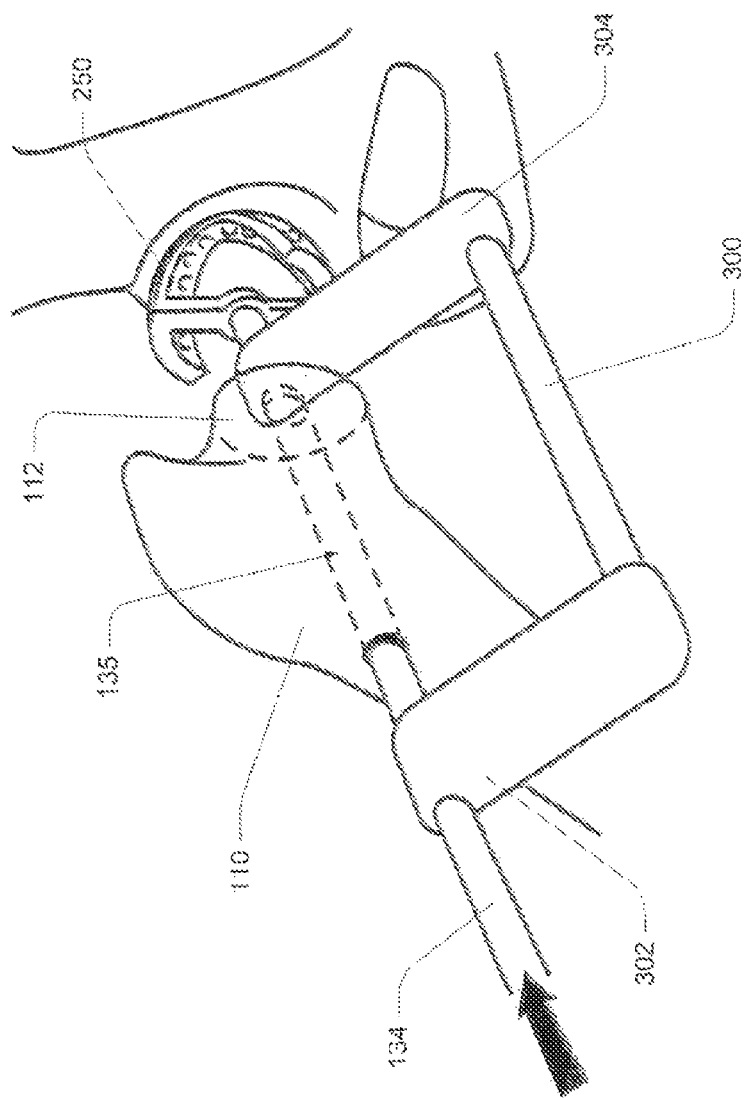
FIG. 11 is a schematic view of the layout of FIG. 1, showing an embodiment acetabulum reamer device coupled to an embodiment outrigger device.

Referring to FIG. 11, an outrigger device 300 can be coupled to femoral elongate element (or femoral rod) 134. A first end 302 of the outrigger device 300 is coupled to the distal end of the femoral elongate element (or femoral rod) 134, and the second end 304 of the outrigger device 300 extends through the anterior incision and is coupled to the acetabular reamer 250. Lateral movement of the outrigger device 300 substantially along the axis of the femoral neck shaft can bring the acetabular reamer 250 into reaming engagement with the acetabulum.

It would be appreciated that the acetabulum can be reamed by pushing the outrigger device 300 in the correct orientation. In an embodiment, the outrigger device 300 can slidably engage the femoral elongate element (or femoral rod) 134, being in the correct orientation.

Figure 12:
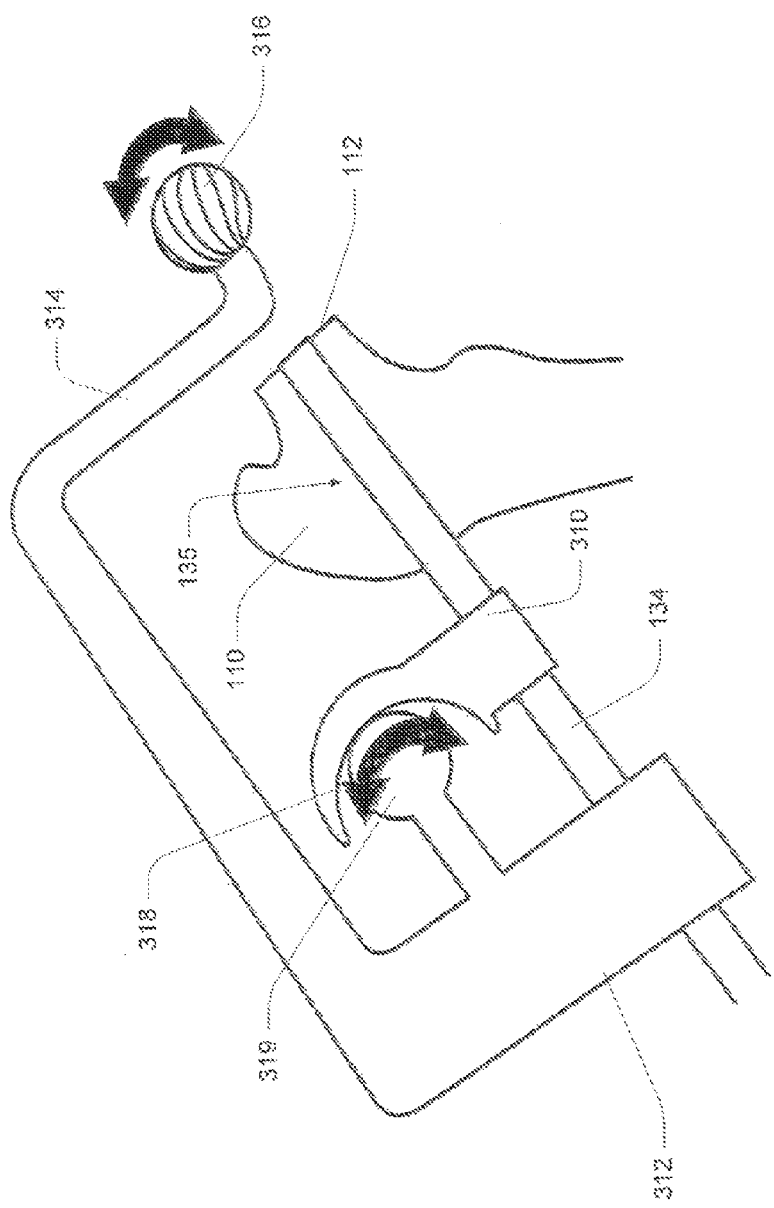
FIG. 12 is a schematic view of the layout of FIG. 1, showing an embodiment acetabulum reamer device coupled to an embodiment outrigger device.

Referring to FIG. 12, an alternative embodiment an outrigger device 310 can be used to prepare the acetabulum. A first end 312 of the outrigger device 310 is coupled to the distal end of the femoral elongate element (or femoral rod) 312, and the second end 314 of the outrigger device 310 extends through the anterior incision and is coupled to an acetabular burr 316. In this example embodiment, outrigger device 310 has a burr guide surface 318 operatively associated with a burr guide element 319, such that movement of the burr guide element 319 along the burr guide surface 318, causes the acetabular burr 316 to move in a corresponding (possibly scaled) motion. In use, the movement of the burr guide element 319 along the burr guide surface 318 causes the acetabular burr 316 to be directed to scribe out the preferred configuration of the acetabulum. In this embodiment, the burr guide element 319 is directed proximally towards the hip joint (when in use). The burr guide surface 318 can be selected to provide a suitable reamed acetabulum configuration.

It will be appreciated that the outrigger device 310 is required to allow three-dimensional movement of the acetabular burr 316 and burr guide element 319, while maintaining axial orientation with the femoral elongate element (or femoral rod) 134. It will be further appreciated that, the distances of movement in a lateral to medial direction would have to be determined prior to burring, visualising the burr guide element 319 can have a smooth ball tipped end abutting the burr guide surface 318 having the shape and configuration of a required acetabulum.

With the acetabulum surface prepared, the femur can be typically be further prepared.

Figure 13:
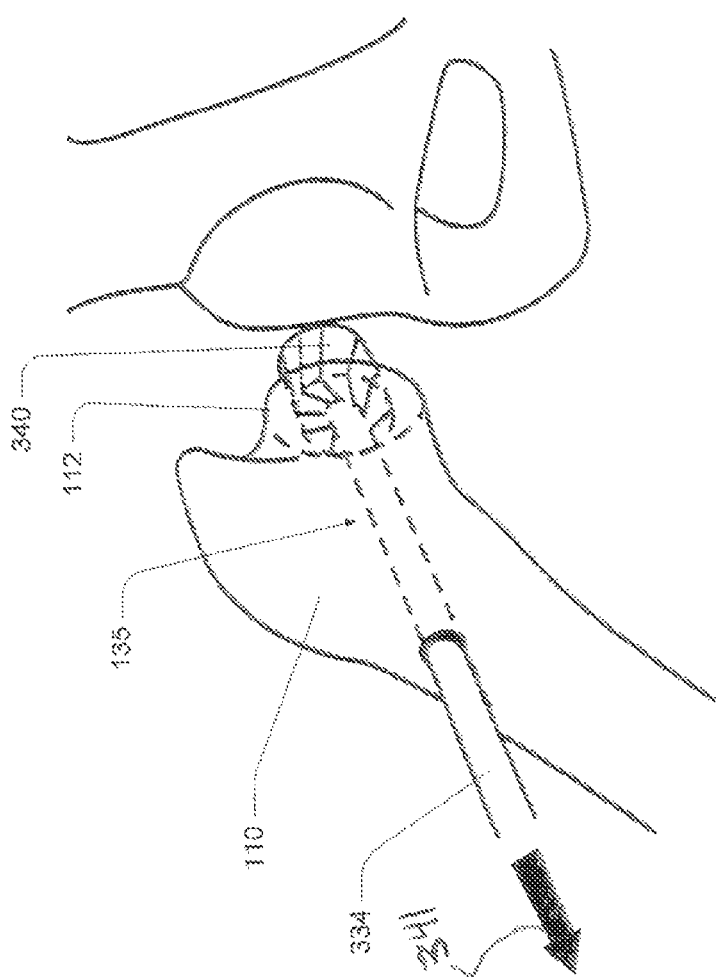
FIG. 13 is a schematic view of the layout of FIG. 1, showing an embodiment femoral reamer device coupled to an embodiment femoral elongate element.

Referring to FIG. 13, a femoral elongate element (or femoral rod) 334 can be placed in the femoral passage and coupled to a femoral reamer 340. It will be appreciated that femoral reamers are sometimes referred to herein as "cavity forming devices." This elongate element 334 can be the same as the femoral elongate element (or femoral rod) 134. The femoral elongate element (or femoral rod) 334 can be threadedly engaged to the femoral reamer 340. It will be appreciated that the femoral neck 112 can be internally reamed to define, for example, a substantially cylindrical femoral cavity, to a required depth, by moving the femoral elongate element 334 in a medial-to-lateral direction (proximal-to-distal), as shown by the arrow indicated by the reference numeral 341, and thereby moving the femoral reamer 340 down into the femoral neck cut. In an embodiment, the femoral elongate element 334 may be rotated about its longitudinal axis by hand or by a surgical drill to rotate the reamer 340. In an embodiment, the femoral elongate element 334 may be pulled in the medial-to-lateral direction by applying a tensile force to the element 334. In an embodiment, the tensile force may be applied to the element 334 by a hammer, such as a slap hammer, or a mallet.

Figure 14B:
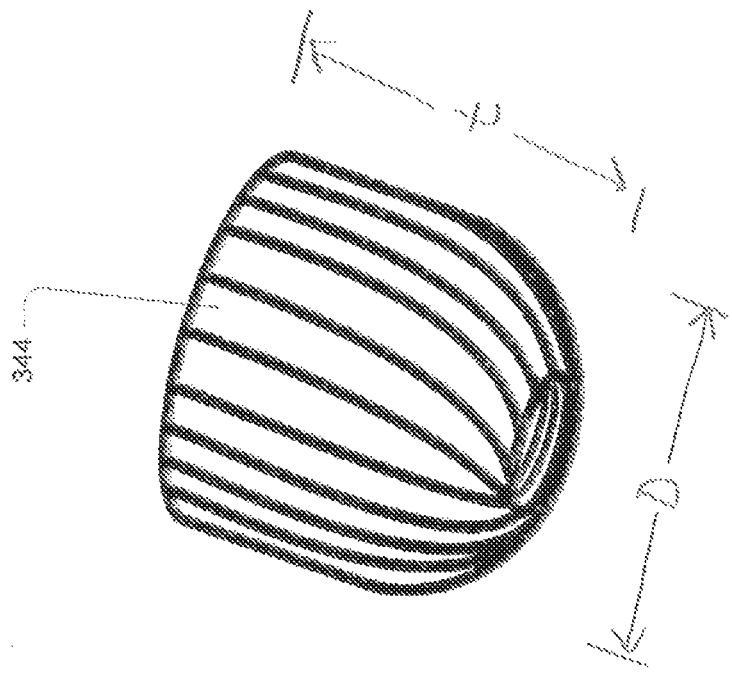
FIG. 14B is a schematic view of an embodiment femoral reamer device.
Figure 14A:
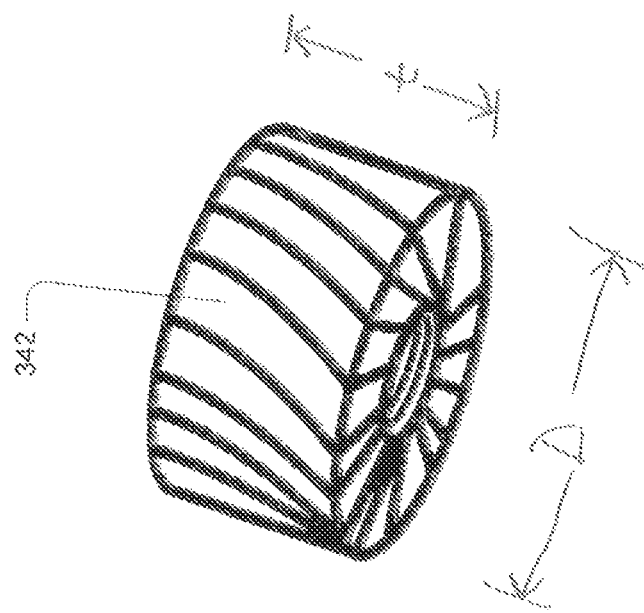
FIG. 14A is a schematic view of an embodiment femoral reamer device.

It will be further appreciated that, by coupling the femoral reamer 340 while located within the hip socket, it is typically not necessary to move or dislocate the hip for enabling internal reaming of the femoral neck 112. It will be appreciated that the femoral reamer 340 can be of a variety of profiles (342, 344) for suitability with an intended prosthetic—as best shown in FIGS. 14A and 14B. In an embodiment, the reamer 342 and 344 may have a diameter, D, between 20 to 40 millimeters and a thickness, t, between 5 to 10 millimeters. Once the femoral neck 112 has been internally reamed, the femoral reamer 340 can then be removed.

FIGS. 15A through 15C show an embodiment femoral reamer 350, which can be used to create a stepped conical femoral cavity 355. This femoral reamer 350 includes a plurality of sleeved burr elements (351, 352, 353). The femoral reamer 350 has a retracted (substantially cylindrical configuration (as shown in FIG. 15A, between 20 to 40 millimeters long), wherein the burr elements can be respectively extended to define a step conical configuration (as shown in FIG. 15B). The burr elements are, by way of example only, concentric with each burr element defining an annulus burr surface, wherein the inner burr element can be drawn distally (e.g. by a coupled to femoral elongate element 334) to thereby extend the femoral reamer 350 into the stepped conical configuration (between 60 to 100 millimeters long). In an embodiment, the femoral elongate element 334 may be moved in the medial-to-lateral direction by applying a tensile force to the element 334. In an embodiment, the tensile force may be applied by a hammer, such as a slap hammer, or a mallet. It will be appreciated that the reamer 350 may be referred to herein as a "cavity forming device."

Figure 16B:
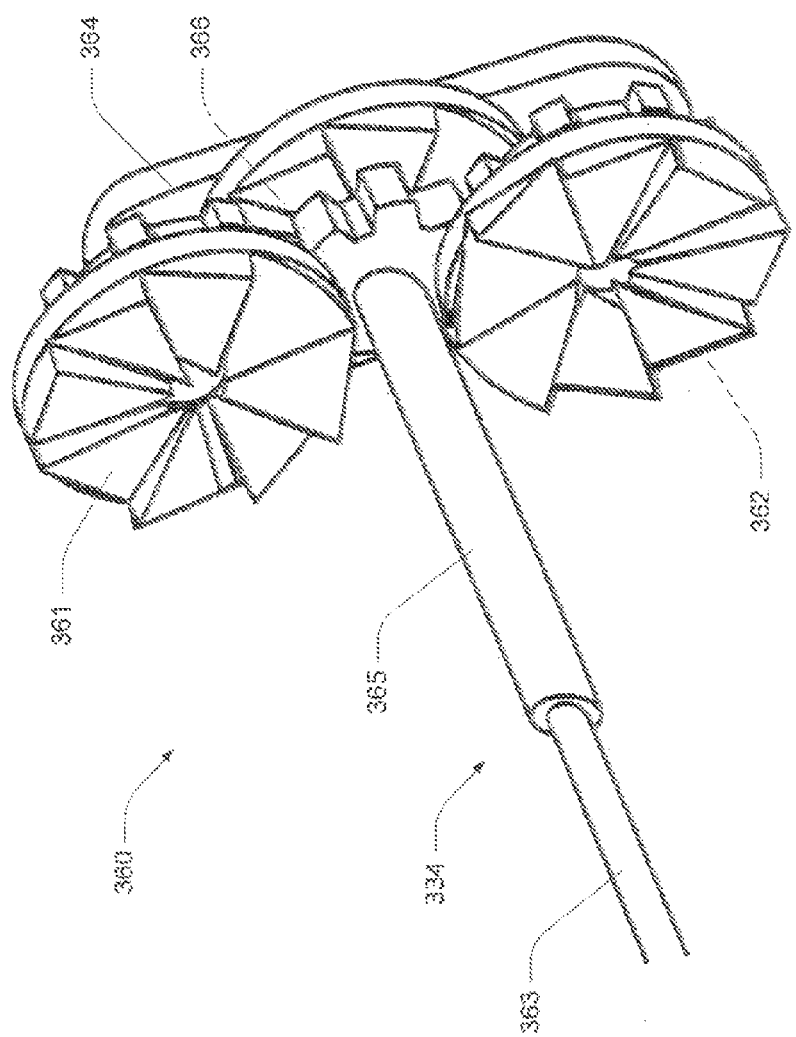
FIG. 16B is a enlarged schematic view of the embodiment femoral reamer device of FIG. 16A.

FIG. 16A and FIG. 16B show an embodiment femoral reamer 360, which can be used to create a femoral cavity having a non-circular cross-section. This example femoral reamer 360 is coupled to an embodiment of a femoral elongate element 334. FIG. 16B shows an enlarged view of an embodiment femoral reamer 360 having a plurality of burr cogs 361, 362. In this embodiment a central shaft 363 is fixed to a backing plate 364 that defined the configuration of the burr cogs 361, 362. The burr cogs 361, 362 are rotatably coupled to the backing plate 364. The central shaft 363 has a rotatable sleeve 365 which is in a geared relationship 366 with one or more of the burr cogs 361, 362, such that rotation of the sleeve 365 with respect to the shaft causes the burr cogs 361, 362 to rotate.

Movement of the burr device towards the bone surface, drawing the femoral elongate element distally, engages the burr cogs 361, 362 with the bone surface to define the femoral cavity. It would be appreciated that the configuration of the burr cogs 361, 362 can be arranged to provide various shaped recesses, for example an oval shape. It would be further appreciated that this device can be used in combination with other recess tools. In an alternative embodiment, the outer sleeve 365 can be fixed to a backing plate and an inner shaft adapted to rotate within the sleeve is in a geared relationship with one or more of the burr cogs.

In an embodiment, the femoral prosthetic attachment portion could be oval or elliptical in shape or cross section. It is possible to prepare any shape using multiple component designs. For example, a femoral reamer (milling) device of FIG. 16B, has two or more rotating circular cogs, of either the same or different diameters, each having a cutting surface on the femoral neck side. There could be provided an outer track with a more complicated design. In an embodiment, the femoral elongate element 334 may be moved in the medial-to-lateral direction by applying a tensile force to the element 334. In an embodiment, the tensile force may be applied by a hammer, such as a slap hammer, or a mallet. It will be appreciated that the reamer 360 may be referred to herein as a cavity forming device.

Figure 17A:
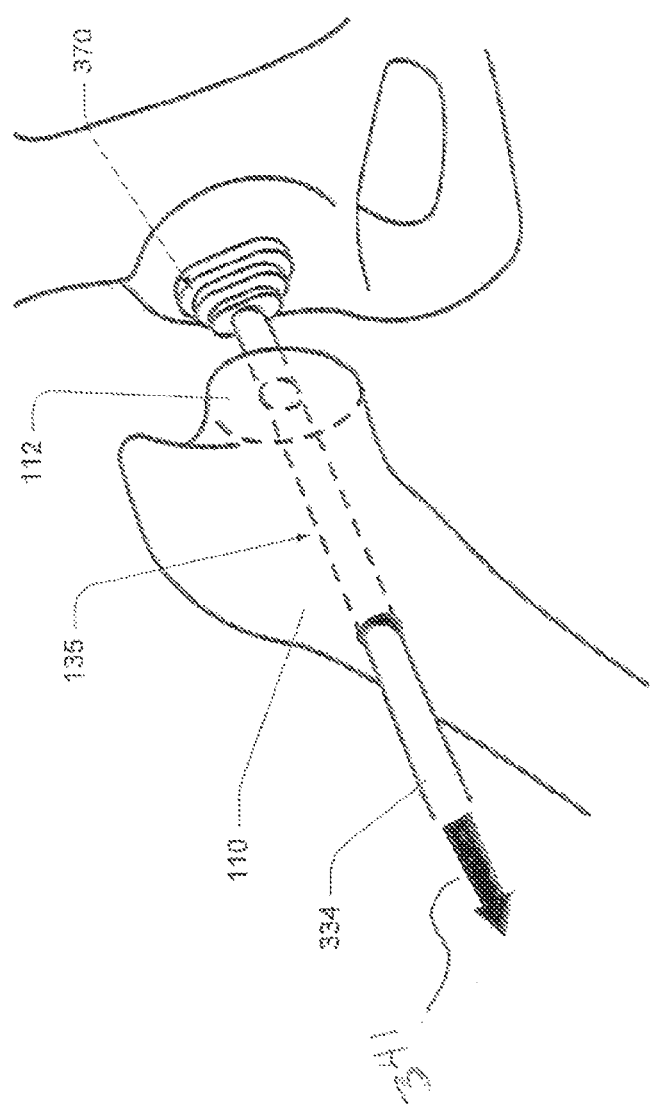
FIG. 17A is a schematic view of the layout of FIG. 1, showing an embodiment femoral reamer device coupled to an embodiment femoral elongate element.

FIG. 17A and FIG. 17B show an embodiment cavity forming device 370, in the form of a bone broach, which can be used to create a femoral cavity having a selected cross-section, such as a circular or non-circular cross section. A femoral elongate element 334 can be threadedly engaged to the cavity forming device 370 (a proximal end of the element 334 may be male threaded and the device 370 may include a female threaded bore). It will be appreciated that a femoral cavity can be created in the femoral neck 112, by moving the femoral elongate element 334 medial-to-lateral (proximal-to-distal) and thereby moving the cavity forming device 370 down into the femoral neck cut. It would be further appreciated that bone broaches may have a variety of shapes/cross-sections. By way of example, a bone broach may be round shaped 371, oval shaped 372, wedged shaped 373 or rectilinear shaped 374—as best shown in FIG. 17B. It would be appreciated that corners of the bone broach would be typically radiused.

Another possibility to prepare the femoral neck cavity is to use a broach type device with outer teeth protrusions to prepare the bone. There may be a need to use a femoral bone broach (or plurality of femoral bone broaches) defining a stepped increase in the size/cross-section—as shown in FIG. 17A. In an embodiment, by way of example only, a femoral reamer or femoral bone broach can be attached to a femoral elongate element (or femoral rod) rod and moved laterally proximal-to distal, or medial-to-lateral (pulled or hit with a mallet, slap hammer or similar device) from outside of the lateral femoral cortex to thereby define a femoral cavity. In this regard, the elongate elements disclosed herein may include a plate or surface such that the plate or surface may be hit with a mallet or slap hammer device in a medial-to-lateral direction. The present disclosure should be understood to include any suitable manner of applying a tensile force, such as tensile force in the direction 341, to the elongate element 334.

In an embodiment, by way of example only, a selected shape/cross-section can be formed by attaching a corresponding femoral bone broach or femoral reamer to a femoral elongate element (or femoral rod) rod and moved in a retrograde manner to cut a femoral cavity having a predetermined cross-section in the remaining femoral neck for receiving a corresponding femoral prosthesis. In an embodiment, cavity forming device 370 may be moved in the medial-to-lateral direction by applying a tensile force to the element 334. In an embodiment, the tensile force may be applied by a hammer, such as a slap hammer, or a mallet. It will be appreciated that the cavity forming device 370 may be referred to herein as a cavity forming device.

FIG. 18 shows that a femoral neck internal femoral reamer 380 can be operatively associated with an outrigger device 390. A first end 392 of the outrigger device 390 is coupled to the distal end of the femoral elongate element (or femoral rod) 334, and the second end 394 of the outrigger device 390 extends through the anterior incision and is coupled to the femoral reamer 380. Lateral movement (proximal-to-distal) of the outrigger device 390 substantially along the axis of the femoral neck shaft can bring the femoral reamer 380 into reaming engagement with the femoral neck 112.

In an embodiment, the reamer 380 may be any one or more of the following:

one of a plurality of different sizes;
comprised of modular portions;
expandable to allow a single reamer to increase reamer size (for example, the initial 'smaller' diameter being sized to pass through the bone passage, and then expanded to the appropriate diameter when in the hip socket); and
telescoping to create a substantially stepped conical femoral cavity.

Figure 19:
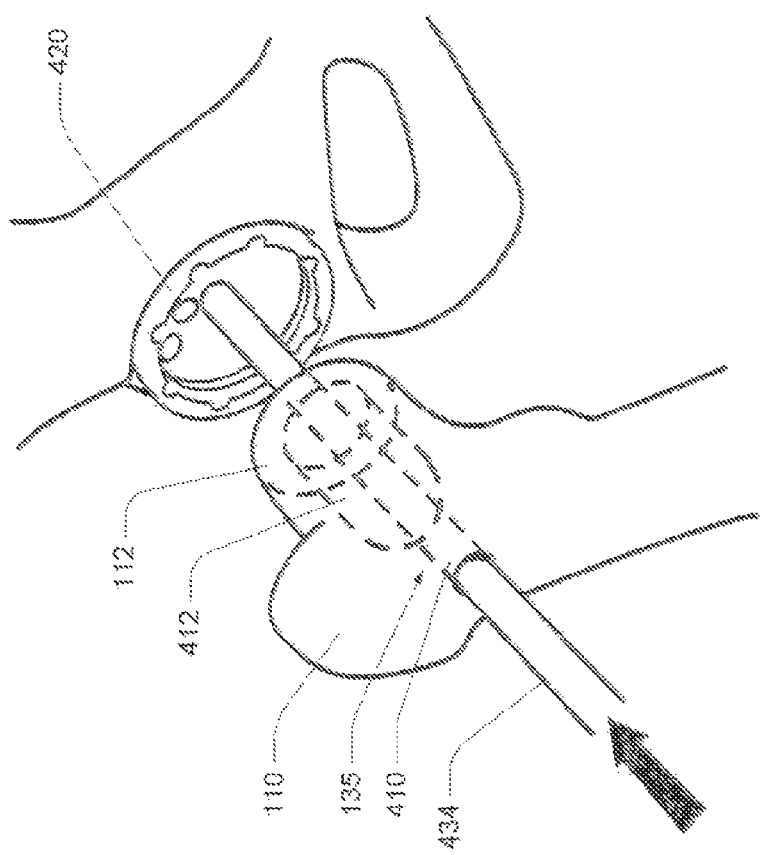
FIG. 19 is a schematic view of the layout of FIG. 1, showing installation of an embodiment acetabular prosthesis.

Referring to FIG. 19, with the femoral passage 410 and femoral cavity 412 prepared, an acetabular component/prosthesis 420 can be inserted through the anterior incision. This acetabular component/prosthesis can be a conventional hemispherical component (or a partial hemispherical component), typically having an inferior cut out to allow easier insertion. This acetabular component/prosthesis 420 can be screwed into place through the femoral passage 410. Screw holes could be created (if required) with a flexible drill. This acetabular component/prosthesis 420 can be impacted into place through the femoral passage 410. The acetabular component 420 can be located into position using a femoral elongate element (or femoral rod) 434.

Figure 20:
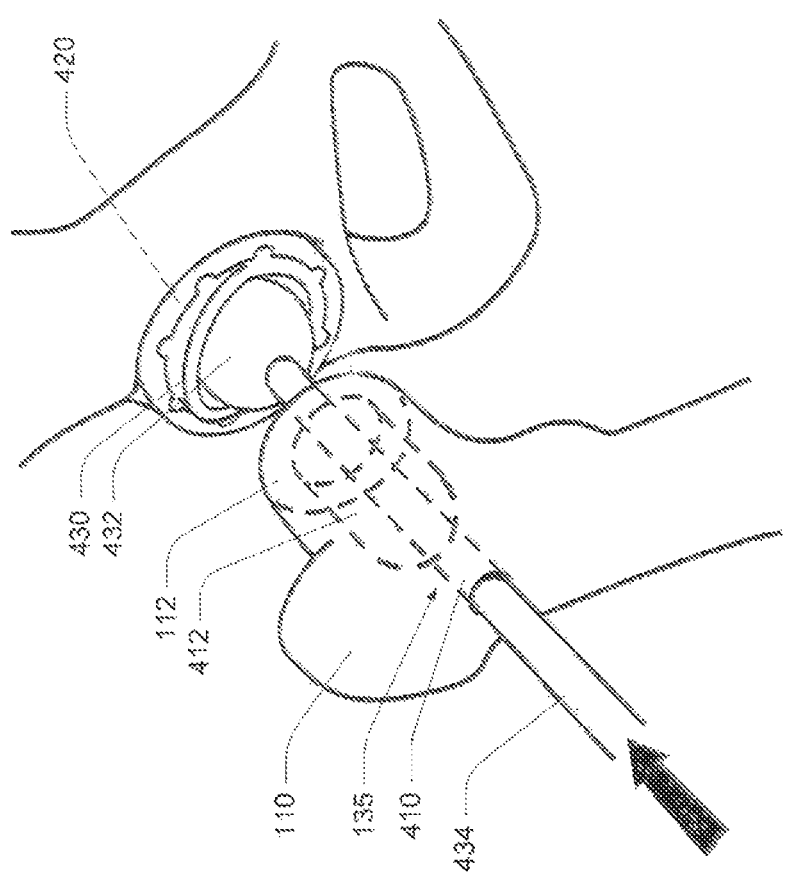
FIG. 20 is a schematic view of the layout of FIG. 1, showing installation of an embodiment acetabular liner element.

Referring to FIG. 20, an acetabular liner element 430 can then be inserted into this acetabular component/prosthesis 420. The acetabular liner 430 may be fixedly coupled or allowed to rotate freely. The acetabular liner 430 would typically be impacted into place with a circular impact head 432 coupled to a femoral elongate element (or femoral rod) 434.

With the acetabular component/prosthesis 420 and acetabular liner 430 installed, installation of a femoral prosthesis can commence. By way of example, a femoral prosthesis can comprise a femoral stem element and a femoral head element, separately or integrated.

Figure 21B:
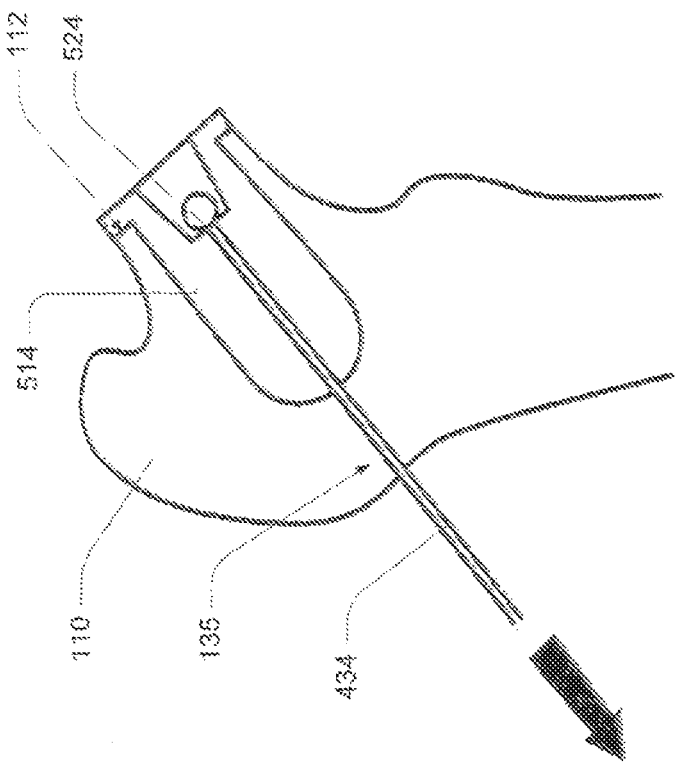
FIG. 21B is a schematic view of a femur, having an embodiment femoral stem element.
Figure 21A:
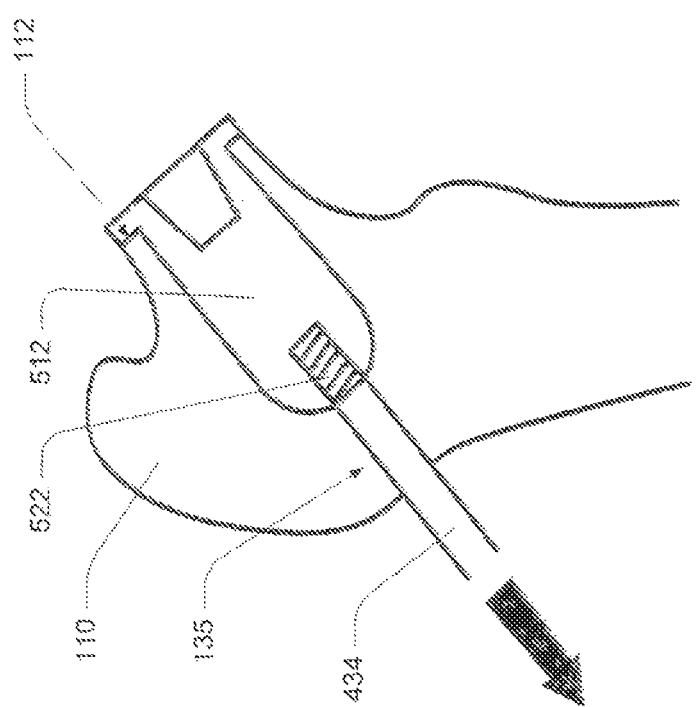
FIG. 21A is a schematic view of a femur, having an embodiment femoral stem element.
Figure 21C:
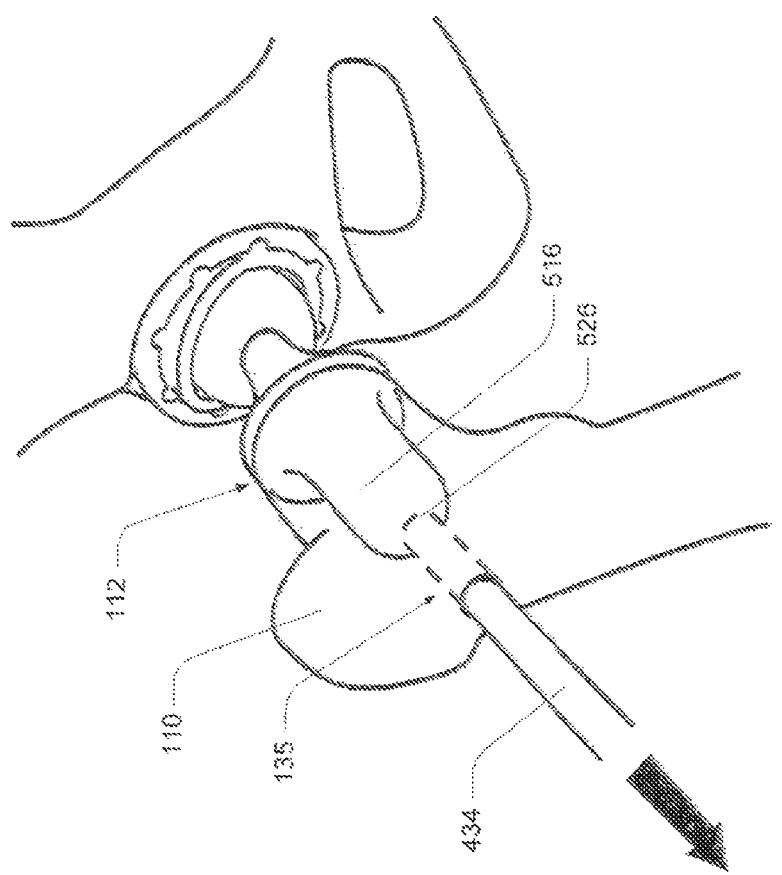
FIG. 21C is a schematic view of a femur, having an embodiment femoral stem element.

Referring to FIGS. 21A through 21C, the femoral stem element 512, 514, 516 can then be inserted through the anterior incision and coupled 522, 524, 526 to a femoral elongate element (or femoral rod) 434. For example, the femoral stem element 512, 514, 516 can be threadedly, abuttingly or otherwise coupled to a femoral elongate element. The femoral stem element 512, 514, 516 is drawn down into a selected position in a retrograde fashion. The lateral end of the femoral elongate element 434 can be drawn laterally (or impacted laterally) in a distal direction to draw the femoral stem element 512, 514, 516 laterally down into the femoral cavity such that when seated it sits in the correct position—typically flush with the cut femoral neck and into the prepared femoral cavity. This component can typically have a flange that is configured to abuttingly engage the neck cut surface or be recessed flush with the neck cut surface or a combination.

It will be appreciated that the femoral stem element 512, 514, 516 could be any one of a plurality of shape configurations. A cylindrical femoral stem element typically includes longitudinal ridges to prevent rotation. A femoral stem element having a flange for fitting atop the femoral neck cut, typically includes protuberances (such as spikes) to further stabilise the femoral prosthesis.

It will be appreciated that the femoral stem element 512, 514, 516 can comprise one or more portions for enabling insertion without dislocating the hip. Portions of the femoral stem element 512, 514, 516 can be coupled or connected. For example, portions of the femoral stem element 512, 514, 516 can be coupled or connected together using any one or more of the following: a screw fixing, a tapered engagement (male to female) or a separate double male connecting rod.

It will be appreciated that, if the femoral stem element 512, 514, 516 is too long to be inserted in an assembled configuration without dislocating the hip, the portions can be placed individually/sequentially into position. Alternatively, the femoral stem element 512, 514, 516 can be inserted as a final procedure of the treatment and require that the leg be rotated to expose more of the femoral neck at this stage.

It will be appreciated that, to draw the femoral stem element 512, 514, 516 down into the femoral neck 112 can use the femoral elongate element (or femoral rod) 434 attach to the femoral stem element 512, 514, 516 as shown in FIG. 21A. In this example the femoral elongate element 434 passed through the femoral passage and threadedly engages the femoral stem element 512, 514, 516. It will be appreciated that other releasable locking/coupling mechanism cab be used. The femoral elongate element (or femoral rod) 434 can be the same elongate element used in other steps of the surgery. Once the femoral stem element 512, 514, 516 has started to enter the femoral cavity in the femoral neck 112, the femoral elongate element 434 can be pulled or hit (slap hammer or attachment to the rod) outside of the lateral cortex of the femur in a retrograde manner (proximal-to distal) for drawing the femoral stem element 512, 514, 516 down into the femoral neck cavity to a final location.

It will be appreciated that, to draw the femoral stem element 514 down into the femoral neck 112 can use a femoral elongate element 434 in the form of a cable with an expanded end element to abut into the stem—as shown in FIG. 21B.

In this example, the femoral elongate element 434 can be passed through the anterior incision and down the femoral passage to abuttingly engage the femoral stem element. Typically, the portion of the femoral elongate element 434 exiting the body about the lateral cortex can have an attachment element (for example a loop) to allow it to be pulled (usually with a slap hammer type device) or engaged to a tensioning device. The femoral elongate element 434 is tensioned for drawing the femoral stem element 514 down into the femoral neck cavity to a final location. The femoral elongate element 434 can be removed through the anterior incision.

Figure 22B:
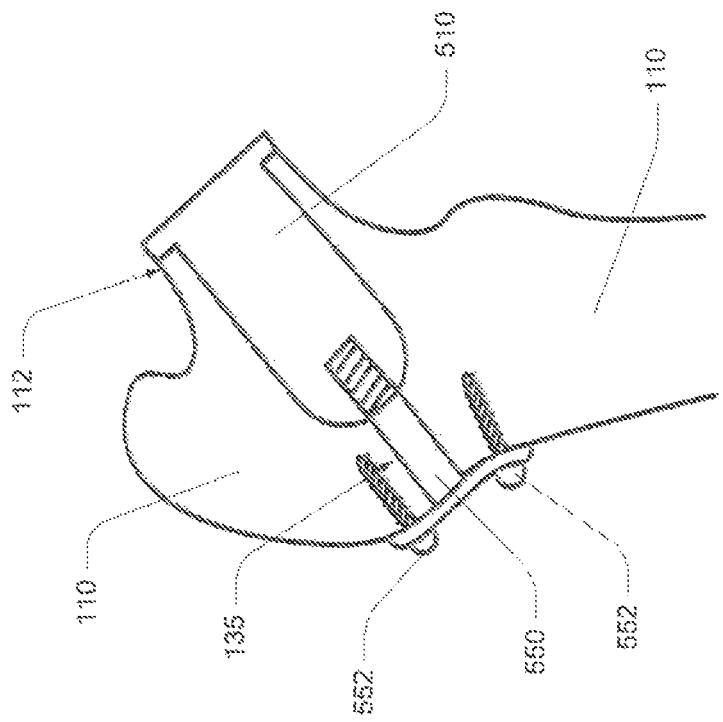
FIG. 22B is a schematic view of a femur, showing fastening of an embodiment femoral stem element.
Figure 22A:
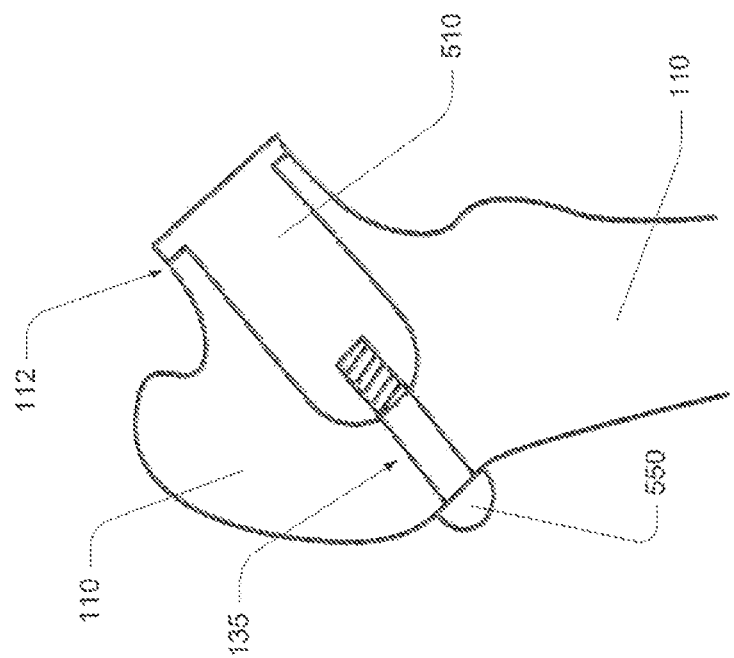
FIG. 22A is a schematic view of a femur, showing fastening of an embodiment femoral stem element.

Referring to FIG. 22A and FIG. 22B, an embodiment femoral stem element 510 can be fixed to the femur. The femoral elongate element (or femoral rod) 434 can be decoupled/disengages (for example unscrewed) from the stem component. A smaller fixing 550 can be passed through the femoral passage 135 and fixed to the femoral stem element 510 for retaining the femoral stem element 510 with respect to the femur 110—as shown in FIG. 22A. In an example embodiment, the fixing fastens at the lateral aspect of the femur, can be in the form of a bolt with a washer or small plate on the outer cortex of the femur for added support. This can improve support and compression fit of the femoral stem element. FIG. 22B shows that further fixings 552 can be applied to a washer or a small plate on the outer cortex of the femur.

It will be appreciated that, if fixings are not required in the femoral passage, a bone graft can be applied. In an embodiment, a femoral stem element can be curved. A curved shape broach could be attached for allow a curved shape femoral stem element. The attachment location on a curved stem would typically be somewhere on the body of the stem rather than the end.

In an embodiment, a femoral stem element can be custom made, requiring custom bone broach/broaches for attaching to the femoral elongate element. In an embodiment, a femoral stem element can have a roughened ingrowth or ongrowth surface. In an embodiment, a femoral stem element can have a plurality of anti-rotational longitudinally fins on its surface for restricting rotation relative to the femoral neck. In an embodiment, a femoral stem element can have a plurality of steps, getting smaller in a graduated fashion from medial-to-lateral to improve stability and migration.

In an embodiment, a femoral stem element can be configured such that the end closest to the lateral cortex may finish abruptly (for example substantially at a right angle) or have a more gentle curved termination. In an embodiment, a femoral stem element can have a flange for abutting the femoral neck, wherein the flange has small protuberances/spikes for restricting rotation relative 25 to the femoral neck.

Figure 23B:
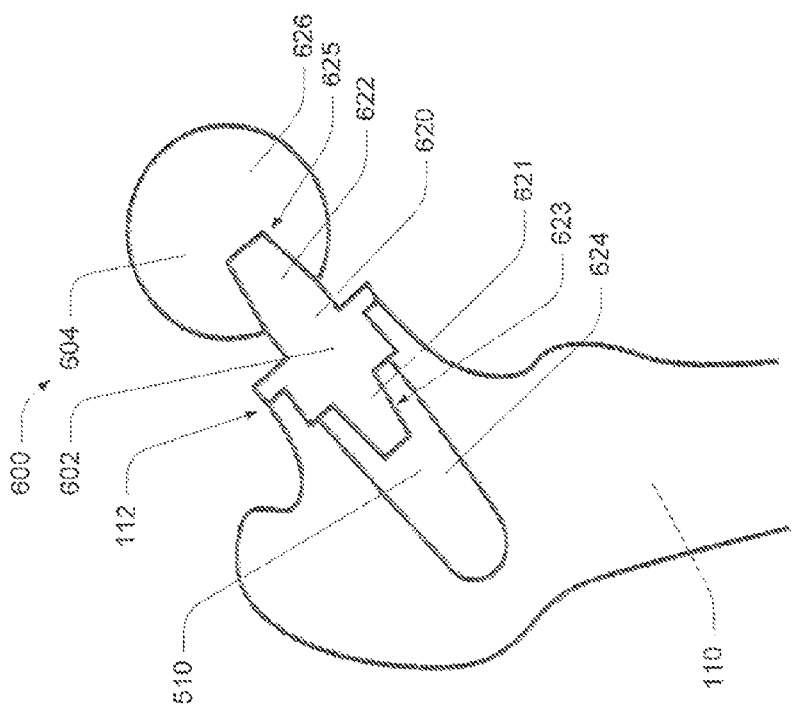
FIG. 23B is a schematic view of a femur—showing installation of an embodiment femoral stem element, femoral neck component and femoral head component.
Figure 23A:
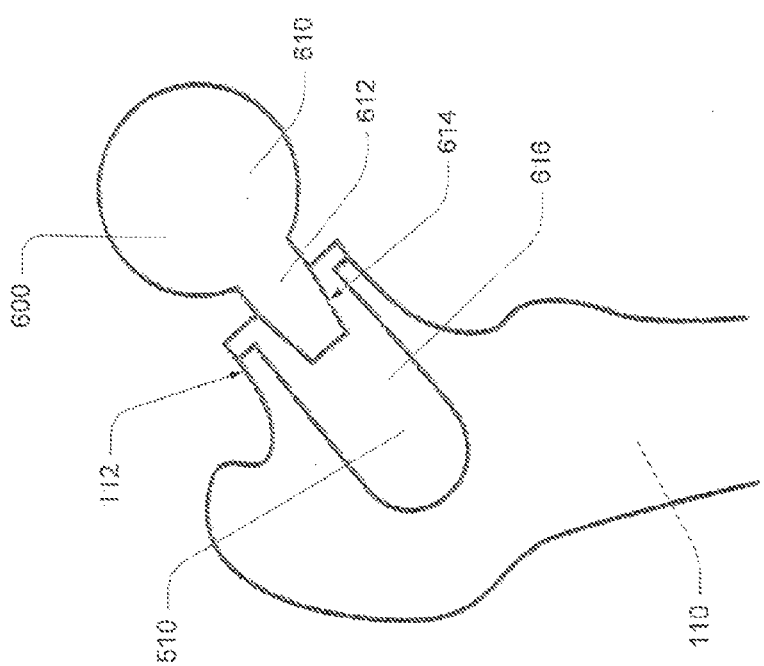
FIG. 23A is a schematic view of a femur—showing installation of an embodiment femoral stem element, femoral neck component and femoral head component.

Referring to FIG. 23A through FIG. 23D, a femoral neck and femoral head component 600 (or components 602,604 respectively) are coupled to the femoral stem element 510. FIG. 23A shows an integrally formed femoral neck head component 610, having a male coupling element 612 engaged to a female coupling element 614 of the femoral stem element 616. FIG. 23B shows a femoral neck component 620, having a pair of oppositely directed male coupling element 621, 622 for each respective engaging a female coupling element 623 of the femoral stem element 624 and a female coupling element 625 of the femoral head component 626. FIG. 23B shows a femoral stem element 630 having an integrally formed male coupling element 632 adapted to be received by a female coupling element 634 of the femoral head component 636.

FIG. 23D shows an integrally formed femoral neck head component 640, having a male coupling element 642 engaged to a female coupling element 644 of the femoral stem element 646. In this example embodiment the male coupling element 642 is rotatable using a polyethylene device 648 in the female coupling element 644. In an example embodiment, a cylindrical outer shell (for example a metal outer shell) houses a polyethylene (or similar material) insert that can rotate in the outer shell in the axis of the femoral neck. A metal rod attached to a femoral head component is located within the polyethylene insert. The metal portion is typically used to strengthen the construct. The head component is attached to (imbedded in) the polyethylene (or other material) liner suitable for allowing rotation.

In an embodiment, a possible construct can comprise a metal rotating inner portion without the polyethylene liner. It will be appreciated that the femoral stem element can have a number of different geometries. Typically the femoral stem element is cylindrical to allow easier reaming, but could be oval or trapezoidal in shape requiring different shaped retrograde reamers. It will be appreciated that the junction coupling associated with a femoral neck and femoral head component can be selected from a variety of configurations, including: male-female taper engagement or female-male taper engagement or a rotatable engagement.

It will be appreciated that, if the femoral neck and femoral head component is too long to be inserted in an assembled configuration without dislocating the hip, the portions can be placed individually/sequentially into position. With the femoral neck and femoral head installed and located within the acetabulum, the traction or restraint of the patent leg/femur can be released and the incisions closed.

Figure 24:
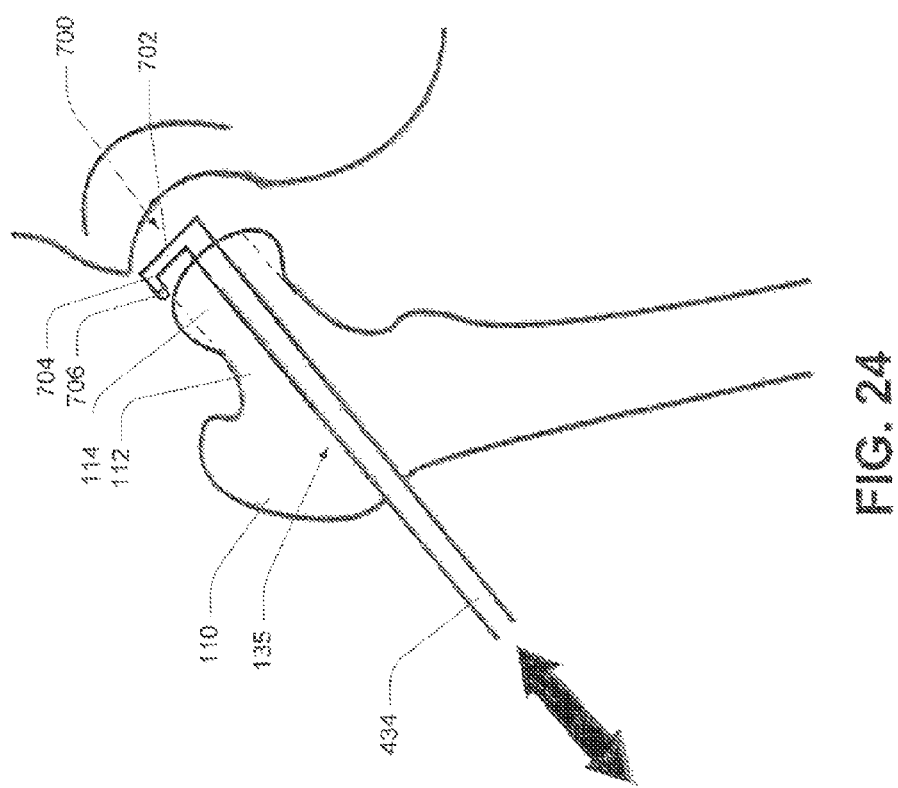
FIG. 24 is a schematic view of the layout of FIG. 1, showing an embodiment femoral head burr element coupled to an embodiment femoral elongate element.

Referring to FIG. 24, the present techniques and methods can be used when resurfacing the femoral head—with or without installation of an acetabulum prosthesis. In an embodiment, by way of example only, a femoral elongate element (or femoral rod) 434 can be coupled to a femoral head burr element (or femoral head reamer 10 element) 700. The femoral head burr element can be passed through the anterior incision and coupled to the femoral elongate element. The femoral head burr element has a radial arm segment 702 to achieve the desired radial dimension of the femoral head for receiving a femoral head prosthesis, and a lateral arm segment 704 to achieve the desired lateral reach for the respective radial distance.

A burr device 706 is located at the lateral extent of the lateral arm segment. The femoral elongate element can be moved laterally and rotated to achieve the desired femoral head configuration for receiving a femoral head prosthesis. One or more femoral head burr elements can be used. The radial arm segment and lateral arm segment can be adjustable. With the femoral head reconfigured to receive a femoral head prosthesis, the femoral head prosthesis can be coupled to a femoral elongate element can drawn down onto the femoral head (in a retrograde fashion). The femoral head prosthesis can be fastened in a manner similar to the method disclosed above for fixing/fastening a femoral stem element.

It will be appreciated that resurfacing procedures or other similar procedures removing and replacing different amounts of the femoral head. For example, mid head resection could be performed with similar techniques. In an example embodiment, after the appropriate amount of femoral head is cut or burred away, a separate burr could be attached at right angles to a femoral elongate element such that the burr end is facing the lateral cortex (away from the acetabulum). This burr could be adjustable typically with a screwdriver such that as the burr is moved more towards (reducing the diameter) the rod more bone is removed to the appropriate size. This burr could be pulled along the rod coming out the lateral cortex and moved by the surgeon in a rotating fashion all the way around the circumference of the head.

In this technique the burr itself is rotating to cut the femoral bone. Where and how much bone is cut is determined by the user, the medial/lateral movement can be measured from the femoral elongate element, the diameter controlled with a screwdriver or ratchet mechanism, with measurement marks on the arm the burr is attached to. A protective shield may be placed on the outer side of this burr to protect the soft tissues.

In an embodiment, a special blade with sharp cutting teeth could be attached to the rod from inside the joint such that it rotates with the rod to cut the bone in a rotating cutting mechanism. In this case the blade is rotating around the femoral head. This could also be adjustable to take increasingly more bone to the appropriate diameter. In an embodiment, a special cylindrical reamer or burr used to ream the remaining portion of the femoral head attached to an outrigger device. This particular reamer could also be adjustable to ream different sized diameters.

Figure 25:
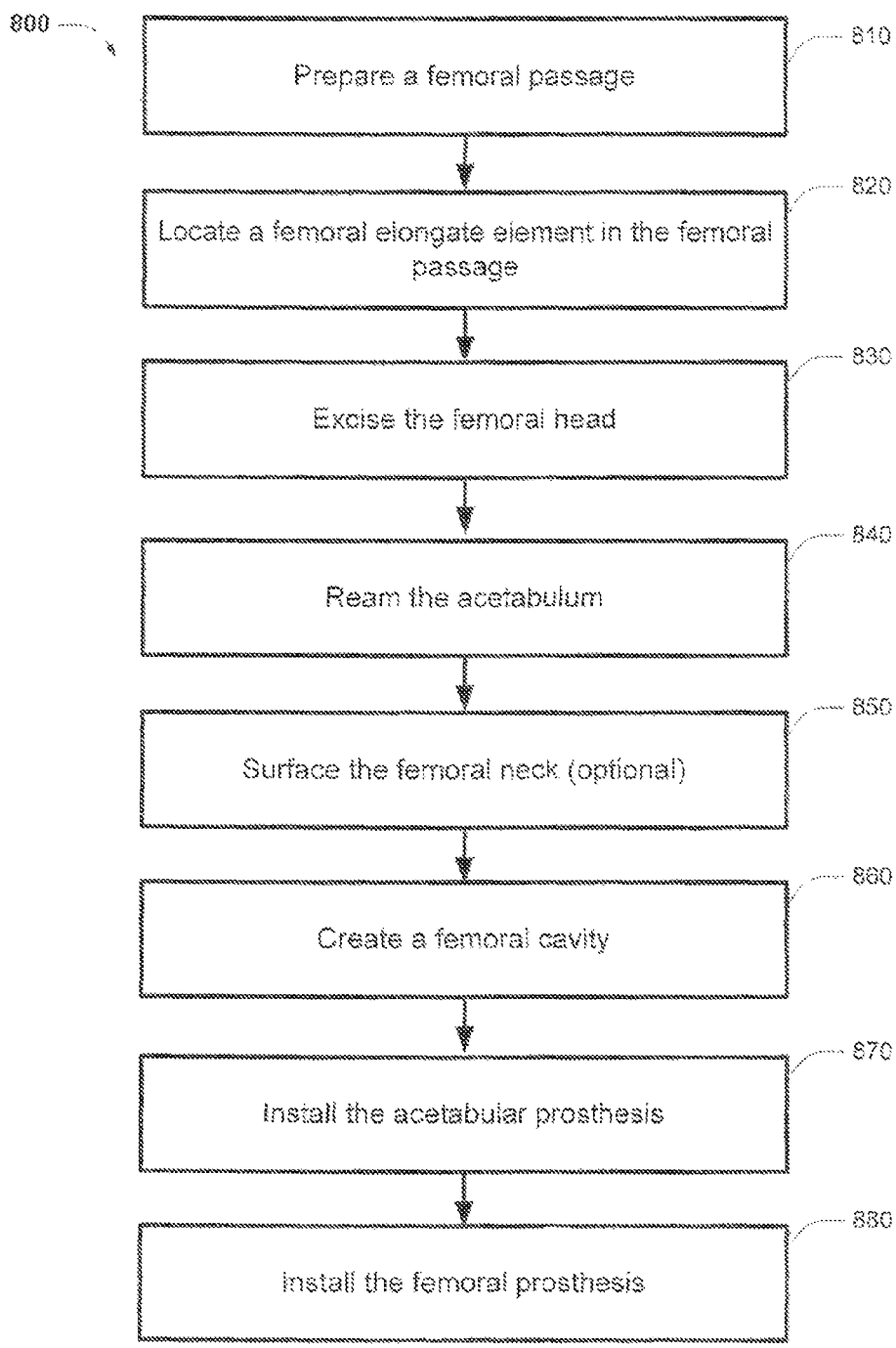
FIG. 25 shows a flowchart for an embodiment method of arthroscopic assisted arthroplasty hip treatment.
Figure 26:
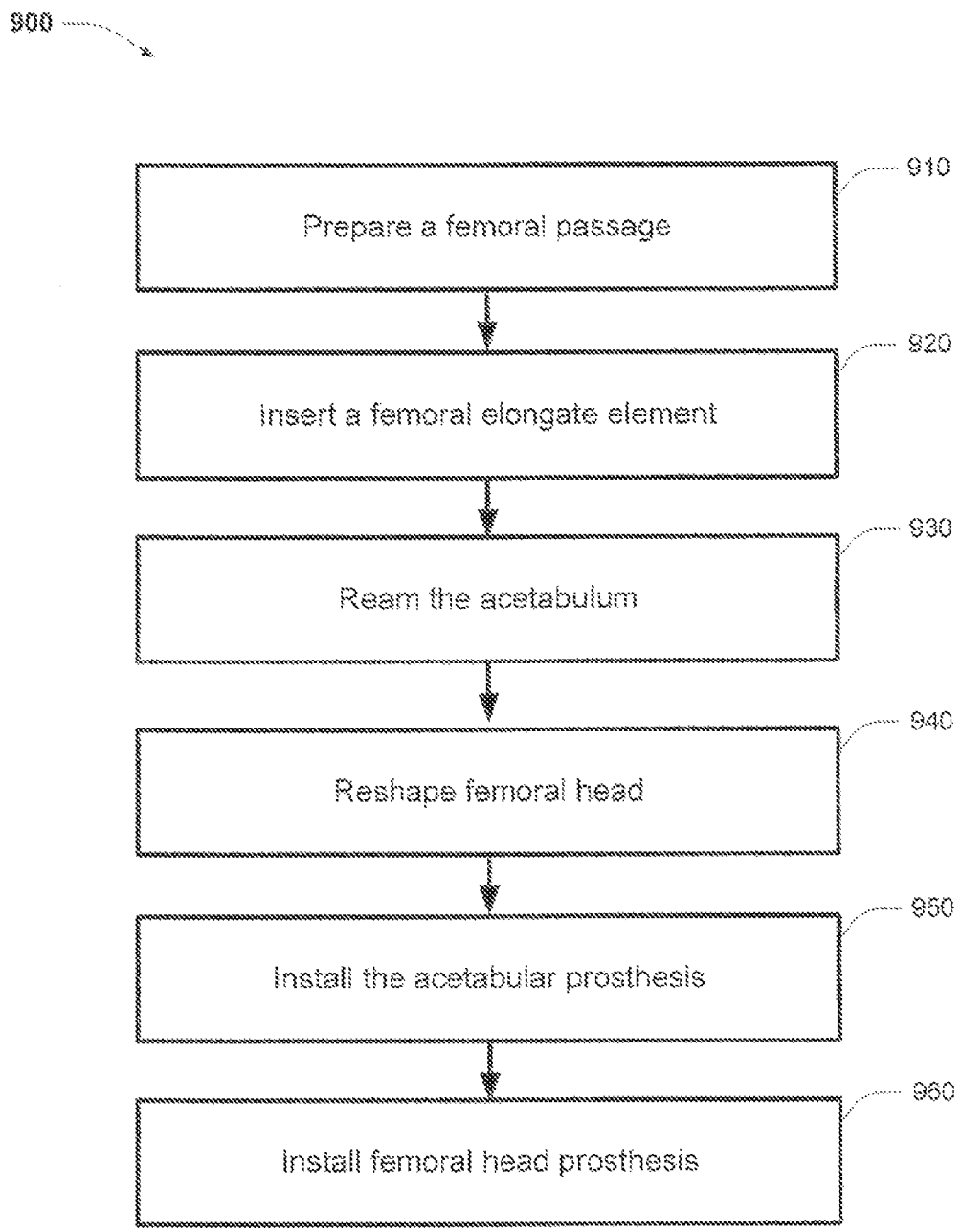
FIG. 26 shows a flowchart for an embodiment method of arthroscopic assisted arthroplasty hip treatment.

Referring to FIG. 25 and FIG. 26, disclose methods for hip replacements according to an embodiment of the present disclosure, including providing an improved less-invasive implantation method of a prosthesis for hip replacements.

FIG. 25 shows a flowchart for an embodiment method 800 of arthroscopic assisted arthroplasty hip treatment. The method may comprise the steps of:

STEP 810: preparing a femoral passage directed along the axis of the femoral neck;
STEP 820: inserting or locating a femoral elongate element in the femoral passage;
STEP 830: excising the femoral head using an excise device fixedly coupled to the femoral elongate element;
STEP 840: reaming the acetabulum using an acetabulum reamer coupled to the femoral elongate element;
STEP 850: optionally, surfacing the femoral neck using a femoral surfacing element coupled to the femoral elongate element;
STEP 860: creating a femoral cavity using a femoral reamer coupled to the femoral elongate element;
STEP 870: installing the acetabular prosthesis using the femoral elongate element; and
STEP 880: installing the femoral prosthesis using the femoral elongate element.

In an embodiment, by way of example only, the method 800 can be defined using the following steps STEP 810-STEP 820: preparing a femoral passage directed along the axis of the femoral neck and inserting or locating a femoral elongate element in the femoral passage—
(a) drilling a femoral guide passage and/or inserting a femoral guide (for example, a wire or a pin) through a lateral incision to define a femoral guide passage;
(b) inserting or locating a femoral elongate element through the lateral incision, the femoral elongate element being located over the femoral guide to a selected depth in the femoral guide passage, for defining a femoral passage;
STEP 830: excising the femoral head using an excise device fixedly coupled to the femoral elongate element—
(a) installing an outrigger device, being fixedly couplable femoral elongate element;
(b) locating and orientating an excise device using the outrigger device for removal of the femoral head;
(c) removing the femoral head using the excise device;
STEP 840: reaming the acetabulum using an acetabulum reamer coupled to the femoral elongate element—
(a) engaging an acetabulum guide to the femoral elongate element located along the femoral guide passage;
(b) manipulating location and orientation of the acetabulum guide to locate the femur relative to the acetabulum for subsequent acetabular reaming;
(c) restraining the femur for subsequent acetabular reaming;
(d) coupling an acetabulum reamer to the femoral elongate element;
(e) reaming the acetabulum;
STEP 850: optionally, surfacing the femoral neck using a femoral surfacing element coupled to the femoral elongate element—
(a) surfacing the femoral neck;
STEP 860: creating a femoral cavity using a femoral reamer coupled to the femoral elongate element—
(a) coupling a femoral reamer to a femoral elongate element;
(b) preparing the femur by creating a femoral cavity to receive a prosthetic femoral head using the femoral reamer;
STEP 870: installing the acetabular prosthesis using the femoral elongate element—
(a) installing the acetabular prosthesis; and
STEP 880: installing the femoral prosthesis using the femoral elongate element—
(a) installing the femoral prosthesis.

It will be appreciated that, in an embodiment all method steps can be made with respect to femoral elongate element protruding from the lateral incision at the outer side of the thigh. Control of the acetabulum reamer and femoral reamer is with respect to the protruding portion of the femoral elongate element. The femoral elongate element is used in installing both the acetabular prosthesis and femoral prosthesis.

FIG. 26 shows a flowchart for an alternative embodiment method 900 of arthroscopic assisted arthroplasty hip treatment. The method comprising the steps of:

STEP 910: preparing a femoral passage directed along the axis of the femoral neck;

STEP 920: inserting or locating a femoral elongate element in the femoral passage;

STEP 930: reaming the acetabulum using an acetabulum reamer coupled to the femoral elongate element;

STEP 940: reshape (reducing the diameter of) the femoral head using a femoral reamer coupled to the femoral elongate element;

STEP 950: installing the acetabular prosthesis using the femoral elongate element; and STEP 960: resurfacing the femoral head with a femoral head prosthesis using the femoral elongate element.

It will be appreciated that the disclosed procedures can have anyone or more of the following advantages:

the procedure can be completed through a relatively small incision with arthroscopic assistance;

the procedure can be completed without full dislocation of the hip;

the procedure is bone sparing;

the procedure can accurately reproduce hip anatomy;

the procedure can maintain alignment of the axis of the femoral neck to axis of the acetabulum.

It will be appreciated that minimal instruments can be used, particularly if custom made. Instruments can include: one acetabular reamer of the correct size, one femoral preparation reamer, a guide wire, an overdrill or femoral reamer, a threaded rod and the prosthesis.

While the above method and apparatus has been described with respect to arthroscopic assisted arthroplasty hip treatment, aspects of the procedure can be suitable for other joints such as the shoulder, ankle or knee. For example, if the method is preformed on the shoulder, drilling would be performed through the lateral aspect of the humerus. For example, if the method is preformed on the ankle, drilling would be performed through the lateral bottom (base) aspect of the calcaneus.

In an embodiment, objects (tools or prosthesis) being placed through the skin incision may have an outer coating (such as a smooth plastics), which can be removed once inside the cavity either arthroscopically or using direct vision/access. The outer coating can have a strong suture or cord attached for assisting removal.

In an embodiment, the femoral elongate element is in the form of an elongate rod shaft or sleeve—being threaded or partially threaded. In an embodiment, the femoral passage can be sleeved, providing a sleeved configuration between femoral passage and femoral elongate element, and enabling lateral and/or rotational movement of the femoral elongate element with respect to the femoral passage. It will be appreciated that the illustrated embodiment disclose methods and apparatus for arthroscopic assisted arthroplasty treatment.

In an embodiment, the present disclosure allows the femur to be prepared in a medial-to-lateral direction, opposite of normal. It will be appreciated that any variation of reamer may be utilized to prepare the femur in a medial-to-lateral direction. In an embodiment, the reamer may include an expanding reamer that can be adjusted at various depths. In an embodiment, the present disclosure may provide robotic burring of both the femur and acetabulum.

In an embodiment, the head prosthesis (or femoral prosthesis or humeral prosthesis) may include a single unitary piece or many modular pieces, e.g., stem, neck, and ball, to allow easier insertion. In an embodiment, a modular head prosthesis may be connected by varying taper junctions and include +/− adjustment screw. Different types of anti-rotation roughenings, linear protrusions, symmetrical, asymmetrical, smaller bumps of different shapes, e.g., semicircles, triangles, may be utilized on the stem. Modular head prostheses may be joined by taper locking mechanisms, threads or a central threaded device.

In an embodiment, the present disclosure allows the shoulder joint, and in particular, the humerus, to be prepared in a medial-to-lateral direction, opposite of normal. In the shoulder, the drill may be passed through the humerus and the humeral head, from the lateral side to prepare the glenoid in the same way as the acetabulum in the hip. The humeral head and neck would then be prepared the same as the femoral head and neck, i.e., from the inside out or in the medial-to-lateral direction. The instruments and components may be inserted through a small anterior incision, preserving the capsule and not dislocating the shoulder. A shoulder prosthesis, including a head prosthesis and a socket prosthesis may be utilized to replace the shoulder joint. The head prosthesis may be modular and include a head and a stem.

As used herein, the term "joint" may refer to a ball and socket joint, which may for example have a socket, and a head disposed on a neck extending from a bone into the socket, including but not limited to the hip joint or the shoulder joint of a patient. As used herein, the term "patient" may refer to a human or an animal. As used herein, the term "head" may refer to the femoral head or the humeral head. As used herein, the term "bone" may refer to the femur or the humerus. As used herein, the term "neck" may refer to the femoral neck or the humeral neck. As used herein, the term "socket" may refer to the acetabulum or the glenoid (or glenoid cavity). As used herein, the term "cavity forming device" may refer to a reamer or broach. As used herein, the term "socket reamer" may refer to an acetabulum reamer or a glenoid reamer.

In an embodiment, a method of repairing a joint of a patient with a head prosthesis and a socket prosthesis, the joint formed by a head disposed on a neck extending from a bone and a socket, may comprise the steps of: (a) preparing a passage directed along an axis of the neck of the bone; (b) resecting the head from the neck to define a neck surface; (c) coupling a cavity forming device onto a proximal end of an elongate element installed in the passage; (d) forming a cavity in the neck surface using the cavity forming device by pulling the cavity forming device in a medial-to-lateral direction by applying a tensile force to the elongate element installed in the passage; (e) reaming the socket using a socket reamer; (f) installing the socket prosthesis into the reamed socket; and (g) installing the head prosthesis into the cavity.

Although the invention has been described with reference to specific examples, it will be appreciated by those skilled in the art that the invention may be embodied in many other forms. Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments. In the claims below and the description herein, any one of the terms comprising, comprised of or which comprises is an open term that means including at least the elements/features that follow, but not excluding others.

Thus, the term comprising, when used in the claims, should not be interpreted as being limitative to the means or elements or steps listed thereafter. For example, the scope of the expression a device comprising A and B should not be limited to devices consisting only of elements A and B. Any one of the terms including or which includes or that includes as used herein is also an open term that also means including at least the elements/features that follow the term, but not excluding others. Thus, including is synonymous with and means comprising.

Similarly, it is to be noticed that the term coupled, when used in the claims, should not be interpreted as being limitative to direct connections only. The terms "coupled" and "connected", along with their derivatives, may be used. It should be understood that these terms are not intended as synonyms for each other. Thus, the scope of the expression a device A coupled to a device B should not be limited to devices or systems wherein an output of device A is directly connected to an input of device B. It means that there exists a path between an output of A and an input of B which may be a path including other devices or means. "Coupled" may mean that two or more elements are either in direct physical, or that two or more elements are not in direct contact with each other but yet still co-operate or interact with each other.

As used herein, unless otherwise specified the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.

As used herein, unless otherwise specified the use of terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader, or with reference to the orientation of the structure during nominal use, as appropriate. Similarly, the terms "inwardly" and "outwardly" generally refer to the orientation of a surface relative to its axis of elongation, or axis of rotation, as appropriate.

Similarly it should be appreciated that in the above description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

An element described herein of an apparatus embodiment is an example of a means for carrying out the function performed by the element for the purpose of carrying out the invention.

In the description provided herein, numerous specific details are set forth. However, it is understood that embodiments of the invention may be practiced without these specific details. In other instances, well-known methods, structures and techniques have not been shown in detail in order not to obscure an understanding of this description. Thus, while there has been described what are believed to be the preferred embodiments of the invention, those skilled in the art will recognize that other and further modifications may be made thereto without departing from the spirit of the invention, and it is intended to claim all such changes and modifications as fall within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

It will be appreciated that an embodiment of the invention can consist essentially of features disclosed herein. Alternatively, an embodiment of the invention can consist of features disclosed herein. The invention illustratively disclosed herein suitably may be practiced in the absence of any element which is not specifically disclosed herein.

It will be appreciated that the structure and apparatus disclosed herein is merely one example of a means for hip arthroplasty, and it should be appreciated that any structure, apparatus or system for hip arthroplasty which performs functions the same as, or equivalent to, those disclosed herein are intended to fall within the scope of a means for hip arthroplasty, including those structures, apparatus or systems for hip arthroplasty which are presently known, or which may become available in the future. Anything which functions the same as, or equivalently to, a means for hip arthroplasty falls within the scope of this element.

Those having ordinary skill in the relevant art will appreciate the advantages provide by the features of the present disclosure. For example, it is a feature of the present disclosure to provide devices, apparatus, and methods for hip replacements. Another feature of the present disclosure to provide such devices, apparatus, and methods for repairing hip joints without dislocating the hip joints.

In the foregoing Detailed Description, various features of the present disclosure are grouped together in a single embodiment for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description of the Disclosure by this reference, with each claim standing on its own as a separate embodiment of the present disclosure.

It is to be understood that the above-described arrangements are only illustrative of the application of the principles of the present disclosure. Numerous modifications and alternative arrangements may be devised by those skilled in the art without departing from the spirit and scope of the present disclosure and the appended claims are intended to cover such modifications and arrangements. Thus, while the present disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A method of replacing a joint of a patient with a head prosthesis and a socket prosthesis, the joint formed by a head disposed on a neck extending from a bone and a socket, the method comprising steps of:
   (a) preparing a passage directed along an axis of the neck of the bone;
   (b) resecting the head from the neck to expose a neck surface on the bone;
   (c) coupling a cavity forming device onto a proximal end of an elongate element installed in the passage;
   (d) forming a cavity in the neck surface using the cavity forming device by applying a tensile force to the elongate element such that the cavity forming device is pulled in a medial-to-lateral direction and into the neck surface;
   (e) coupling a surface preparation device to a femoral side of a socket reamer, and coupling the surface preparation device and the socket reamer to a proximal end of the elongate element installed in the passage;
   (f) reaming the socket using the socket reamer;
   (g) installing the socket prosthesis into the reamed socket; and
   (h) installing the head prosthesis into the cavity formed in the neck surface.

2. The method of claim 1, wherein step (b) comprises resecting the head from the neck using an excise device.

3. The method of claim 2, further comprising excising the head from the neck using a cutting guide coupled to an elongate element installed in the passage.

4. The method of claim 3, further comprising inserting a guide aperture of the cutting guide onto a distal end of the elongate element.

5. The method of claim 4, wherein the cutting guide further comprises an arm portion and a cutting guide slot, wherein the arm portion is interposed between the cutting guide slot and the guide aperture.

6. The method of claim 5, further comprising positioning the cutting guide slot over the neck by locating the guide aperture along a longitudinal axis of the elongate element.

7. The method of claim 6, further comprising inserting the excise device through the cutting guide slot and using the excise device to excise the head.

8. The method of claim 1, wherein the surface preparation device comprises an abrading surface facing towards a distal end of the elongate element.

9. The method of claim 8, wherein the surface preparation device comprises a substantially planar abrading surface.

10. The method of claim 9, wherein the surface preparation device and the socket reamer are coupled back-to-back.

11. The method of claim 1, wherein the head prosthesis comprises a stem, and the method further comprises installing the stem of the head prosthesis into the cavity using a tensile force applied to an elongate element installed in the femoral passage and coupled to the stem.

12. The method of claim 11, wherein the elongate element coupled to the stem comprises one of a rod and a cable.

13. The method of claim 1, further comprising positioning the bone using a socket guide device coupled to a proximal end of an elongate element installed in the passage, wherein the socket guide device is installed into the socket to align the bone with respect to the socket.

14. The method of claim 1, wherein the socket reamer comprises a guide aperture, an arm portion and a reaming head, wherein the arm portion extends between the guide aperture and the reaming head and the guide aperture is configured and dimensioned to receive a distal end of an elongate element installed in the passage.

15. The method of claim 1, wherein step (a) comprises using a surgical drill to form the passage in a lateral-to-medial direction.

16. The method of claim 1, wherein the passage extends from an outer side of the bone and through an apex of the head.

17. The method of claim 1, further comprising securing the socket prosthesis in the reamed socket with fasteners using a drive shaft extending through the passage.

18. The method of claim 1, wherein all of steps are performed without dislocating the joint.

19. The method of claim 1, wherein the socket reamer comprises a bone side and a socket side, the bone side having a perimeter and a female threaded passageway; wherein the bone side further comprises a slot extending between the perimeter and the female threaded passageway, wherein the slot is configured and dimensioned to allow passage of a guide wire or a guide pin.

20. The method of claim 1, wherein the joint is a hip joint, the bone is the femur, and the socket is the acetabulum.

21. The method of claim 1, wherein the joint is a shoulder joint, the bone is the humerus, and the socket is the glenoid.

22. The method of claim 1, wherein the cavity forming device is one of a reamer and a broach.

23. The method of claim 1, wherein the head prosthesis is modular and comprises a stem portion and a ball portion.

24. The method of claim 1, wherein the tensile force is applied to the elongate element coupled to the cavity forming device using a slap hammer or a mallet.

25. The method of claim 1, wherein the cavity has one of a circular cross section and a non-circular cross section.

26. The method of claim 1, wherein step (f) further comprises installing the socket prosthesis into the reamed socket in a medial-to-lateral direction.

27. The method of claim 1, further comprising:
   preparing the neck surface while moving the surface preparation device in the medial-to-lateral direction using a tensile force applied to the elongate element.

28. A method of replacing a hip joint with a femoral prosthesis and an acetabular prosthesis, the hip joint formed by a femoral head connected to a femoral neck extending from a femoral shaft and an acetabulum, the method comprising steps of:
   making a first incision at the hip joint and making a second incision at a lateral side of a thigh;
   preparing a femoral passage directed along an axis of the femoral neck;
   installing a femoral elongate element into the femoral passage through the second incision;
   installing a cutting guide onto the femoral elongate element by inserting an aperture of the cutting guide onto a distal end of the femoral elongate element and sliding the cutting guide into position in a lateral-to-medial direction such that a cutting guide slot of the cutting guide is positioned over the femoral neck;
   inserting an excise device through the cutting guide slot of the cutting guide and excising the femoral neck through the first incision to expose a neck surface;

installing a guide wire or guide pin into the femoral passage;

inserting an acetabulum guide device through the first incision and installing the acetabulum guide device onto a proximal end of a femoral elongate element using the guide wire or guide pin to align the acetabulum guide device and the femoral elongate element;

aligning the femoral shaft relative to the acetabulum using the acetabulum guide device;

restraining the femoral shaft in position as located by the acetabulum guide device;

coupling an acetabulum reamer to a femoral elongate element installed in the femoral passageway using a guide wire or guide pin to align the acetabulum reamer with the femoral elongate element;

reaming the acetabulum using the acetabulum reamer;

coupling a surface preparation device to a proximal end of a femoral elongate element installed in the femoral passage, the surface preparation device having an abrading surface facing towards a distal end of the femoral elongate element;

preparing the neck surface while moving the surface preparation device in a medial-to-lateral direction using a tensile force applied to the femoral elongate element;

coupling a cavity forming device to a femoral elongate element installed in the femoral passageway;

forming a femoral cavity in the neck surface using the cavity forming device by applying a tensile force to the femoral elongate element;

installing the acetabular prosthesis in the reamed actetabulum; and installing the femoral prosthesis into the femoral cavity formed in the neck surface.

29. The method of claim 28, wherein all of the steps are performed without dislocating the hip joint.

30. The method of claim 28, wherein the acetabulum reamer comprises a femoral side, the femoral side having a perimeter and a bore; wherein the femoral side comprises a slot extending between the perimeter and the bore, wherein the slot is configured and adapted to receive the guide wire or guide pin.

31. The method of claim 28, wherein the excise device is a saw blade.

32. The method of claim 28, wherein the acetabulum guide device comprises a semi-spherical outer surface.

33. The method of claim 28, wherein the femoral elongate element onto which the cutting guide is installed, the femoral elongate element onto which the acetabulum guide device is installed, the femoral elongate device onto which the acetabulum reamer is installed, the femoral elongate element onto which the femoral surfacing element is installed, and the femoral elongate element onto which the cavity forming device is installed, are the same femoral elongate element.

34. The method of claim 28, wherein the surface preparation device comprises a distal surface and a proximal surface, wherein a thickness between the distal surface and the proximal surface is about 2 to 10 millimeters.

35. The method of claim 34, wherein the abrading surface comprises a diameter, wherein the diameter of the abrading surface is about 20 to 40 millimeters.

36. The method of claim 35, wherein a ratio of the thickness and the diameter is between 0.05 and 0.5.

* * * * *